United States Patent [19]

Karrer

[11] Patent Number: 5,663,453

[45] Date of Patent: Sep. 2, 1997

[54] DIOXOLANE DERIVATIVES

[75] Inventor: Friedrich Karrer, Zofingen, Switzerland

[73] Assignee: Ciba-Geigy Corporation, Tarrytown, N.Y.

[21] Appl. No.: 373,910

[22] Filed: Jan. 17, 1995

Related U.S. Application Data

[63] Continuation of Ser. No. 23,986, Feb. 26, 1993, abandoned.

[30] Foreign Application Priority Data

Mar. 2, 1992 [CH] Switzerland ................... 643/92

[51] Int. Cl.$^6$ ................... C07C 43/29; C07C 43/263
[52] U.S. Cl. ................... 568/637; 568/48; 568/333; 568/638; 568/811; 568/812
[58] Field of Search ................... 568/48, 333, 637, 568/638, 811, 812

[56] References Cited

U.S. PATENT DOCUMENTS

| | | | |
|---|---|---|---|
| 4,007,280 | 2/1977 | Karrer | 424/278 |
| 4,097,581 | 6/1978 | Farooq et al. | 424/278 |
| 4,590,282 | 5/1986 | Henrick | 549/453 |
| 4,971,981 | 11/1990 | Karrer | 514/336 |

FOREIGN PATENT DOCUMENTS 0458361  11/1991  European Pat. Off. .

*Primary Examiner*—Ba K. Trinh
*Attorney, Agent, or Firm*—Edward McC. Roberts; Marla J. Mathias; William A. Teoli, Jr.

[57]  ABSTRACT

Compounds of the formula

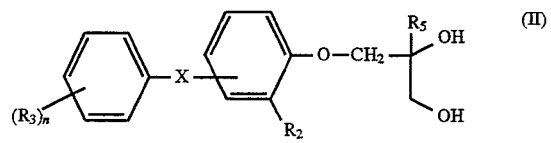

in which:

n is 0, 1 or 2, and, if n is 2, the two radicals $R_3$ are identical or different;

$R_2$ is methyl, fluorine, chlorine or bromine;

$R_3$ is $C_1$–$C_3$-alkyl, halo-$C_1$–$C_3$alkyl, $C_1$–$C_3$alkoxy, halo-$C_1$–$C_3$alkoxy, fluorine, chlorine or bromine;

$R_5$ is hydrogen or $C_1$–$C_9$alkyl and

X is methylene, O, S or C(=O):

can be used as intermediates for agrochemical active ingredients.

4 Claims, No Drawings

DIOXOLANE DERIVATIVES

This a continuation of Ser. No. 08/023,986 filed on Feb. 26, 1993, now abandoned.

The invention relates to compounds of the formula

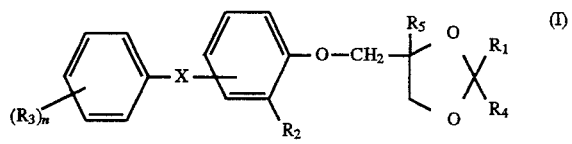

in which:

n is 0, 1 or 2, and, if n is 2, the two radicals $R_3$ are identical or different; either $R_1$ is $C_1$–$C_6$alkyl, halo-$C_1$–$C_3$alkyl, $C_2$–$C_4$alkenyl, $C_2$–$C_4$alkynyl, $C_1$–$C_3$alkoxy or $C_3$–$C_6$cycloalkyl and $R_4$ is hydrogen or $C_1$–$C_3$alkyl, or $R_1$ and $R_4$ together with the carbon atom to which $R_1$ and $R_4$ are bonded are a ring having 4, 5 or 6 ring members, and the ring skeleton, which may contain a carbon-carbon double bond, is composed either only of carbon atoms or of 1 oxygen atom and 3, 4 or 5 carbon atoms, and the ring is unsubstituted or mono- or disubstituted by identical or different $C_1$–$C_3$alkyl radicals;

$R_2$ is $C_1$–$C_3$alkyl, halo-$C_1$–$C_3$alkyl, $C_1$–$C_3$alkoxy, halo-$C_1$–$C_3$alkoxy, fluorine, chlorine or bromine;

$R_3$ is $C_1$–$C_3$alkyl, halo-$C_1$–$C_3$alkyl, $C_1$–$C_3$alkoxy, halo-$C_1$–$C_3$alkoxy, fluorine, chlorine or bromine;

$R_5$ is hydrogen or $C_1$–$C_3$alkyl and

X is methylene, O, S or C(=O), to a process for the preparation and to the use of these compounds, to pesticides whose active ingredient is selected from these compounds, to a process for the preparation and to the use of these compositions and to intermediates for the preparation of the compounds of the formula I.

Unless otherwise defined, the general terms used hereinbefore and hereinafter are as defined below.

The halogen atoms which are suitable as substituents of haloalkyl and haloalkoxy are fluorine and chlorine as well as bromine and iodine, with fluorine, chlorine and bromine being preferred.

Carbon-containing groups and compounds contain, unless otherwise defined, in each case preferably 1 up to and including 4, in particular 1 or 2, carbon atoms.

$C_3$–$C_6$Cycloalkyl is cyclopropyl, cyclobutyl, cyclopentyl or cyclohexyl.

Alkyl—as a group per se and as a structural element of other groups and compounds such as alkoxy, haloalkyl and haloalkoxy—is, in each case with due consideration of the specific number of carbon atoms in the respective group or compound, either straight-chain or branched and is methyl, ethyl, propyl, isopropyl, butyl, isobutyl, sec-butyl or tert-butyl, or pentyl, hexyl, octyl or in each case one of their isomers. Preferred alkyl groups $R_1$ are $C_1$–$C_3$alkyl groups, in particular $C_2$–$C_3$alkyl groups.

Alkenyl and alkynyl contain one or more, preferably not more than two, unsaturated carbon-carbon bonds. Examples which may be mentioned are vinyl, allyl, methallyl, prop-1-en-1yl,2-methyl-prop-1-en-1-yl, but-2-en-1-yl, ethynyl, propargyl, prop-1-yn-1-yl and but-1-yn-1-yl.

Halogen-substituted groups, i.e. haloalkyl and haloalkoxy, can be part-halogenated or perhalogenated: Examples of haloalkyl—as a group per se and as a structural element of other groups and compounds such as haloalkoxy—are methyl which is monosubstituted to trisubstituted by fluorine, chlorine and/or bromine, such as $CHF_2$ or $CF_3$; ethyl which is monosubstituted to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; and propyl or isopropyl, each of which is monosubstituted to heptasubstituted by fluorine, chlorine and/or bromine, such as $CH_2CHBrCH_2Br$, $CF_2CHFCF_3$, $CH_2CF_2CF_3$ or $CH(CF_3)_2$.

The following are preferred within the scope of the invention:

(1) Compounds of the formula

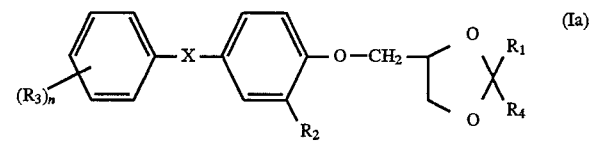

in which:

n is 0, 1 or 2, and, if n is 2, the two radicals $R_3$ are identical or different;

$R_1$ is $C_1$–$C_4$alkyl, vinyl or cyclopropyl;

$R_2$ is methyl or chlorine;

$R_3$ is methyl, fluorine or chlorine;

$R_4$ is hydrogen or methyl and

X is oxygen or methylene;

(2) Compounds of the formula Ia in which X is oxygen, in particular those in which X is oxygen and $R_2$ is chlorine, very particularly those in which X is oxygen, $R_2$ is chlorine and $R_4$ is hydrogen, especially those in which X is oxygen, $R_2$ is chlorine, $R_4$ is hydrogen and $R_1$ is $C_1$–$C_4$alkyl;

(3) Compounds of the formula Ia in which $R_2$ is chlorine;

(4) Compounds of the formula Ia in which $R_4$ is hydrogen, in particular those in which $R_4$ is hydrogen and X is oxygen;

(5) Compounds of the formula Ia in which $R_1$ is $C_1$–$C_4$alkyl, in particular those in which $R_1$ is $C_1$–$C_4$alkyl and X is oxygen, especially those in which $R_1$ is $C_1$–$C_4$alkyl, X is oxygen and $R_2$ is chlorine;

(6) Compounds of the formula Ia according to the above-defined groups (1) to (5) in which n is 0, 1 or 2 and $R_3$ is fluorine or chlorine, in particular those in which n is 1 or 2 and $R_3$ is fluorine or chlorine, especially those in which n is 1 and $R_3$ is fluorine or chlorine;

(7) Compounds of the formula Ia according to the above-defined groups (1) to (6) in which n is 1 and the radical $R_3$ is bonded in the 3- or 4-position, or n is 2 and the radicals $R_3$ are bonded in the 2,4-, 3,4- or 3,5-position, in particular those in which n is 1 and the radical $R_3$ is bonded in the 3-position, or n is 2 and one of the radicals $R_3$ is bonded in the 3-position, especially those in which n is 1 and the radical $R_3$ is bonded in the 3-position, or n is 2 and the radicals $R_3$ are bonded in the 3,4- or 3,5-position;

(8) Compounds of the formula Ia in which X is methylene, $R_2$ is chlorine and $R_4$ is hydrogen, in particular those in which X is methylene, $R_2$ is chlorine, $R_4$ is hydrogen and $R_1$ is $C_1$–$C_4$alkyl;

(9) Compounds of the formula Ia according to the above-defined group (8) in which n and $R_3$ are as defined in the above-defined groups (6) and (7);

(10) Compounds of the formula I in which $R_5$ is hydrogen;

(11) Compounds of the formula I in which the $(R_3)_nC_6H_{5-n}X$ group is bonded in the para-position relative to $R_2$ or to the dioxolanylmethoxy group, in particular in the para-position relative to the dioxanylmethoxy group;

(12) Compounds of the formula I in which the two radicals $R_1$ and $R_4$ are not linked to one another.

Particularly preferred within the scope of the invention are the compounds of the formula I which are mentioned in Examples H3 and H4.

Individually preferred within the scope of the invention are the following compounds of the formula I:

4-(2-chloro-4-phenoxyphenoxymethyl)-2-ethyl-1,3-dioxolane;

4-(2-chloro-4-phenoxyphenoxymethyl)-2-propyl-1,3-dioxolane;

4-(2-chloro-4-phenoxyphenoxymethyl)-2-isopropyl-1,3-dioxolane;

4-(2-chloro-4-phenoxyphenoxymethyl)-2-cyclopropyl-1,3-dioxolane;

4-[2-chloro-4-(3-fluorophenoxy)phenoxymethyl]-2-ethyl-1,3-dioxolane;

4-[2-chloro-4-(3-fluorophenoxy)phenoxymethyl]-2-propyl-1,3-dioxolane;

4-[2-chloro-4-(3-fluorophenoxy)phenoxymethyl]-2-isopropyl-1,3-dioxolane;

4-[2-chloro-4-(3-fluorophenoxy)phenoxymethyl]-2-cyclopropyl-1,3-dioxolane;

4-[2-chloro-4-(3-chlorophenoxy)phenoxymethyl]-2-ethyl-1,3-dioxolane;

4-[2-chloro-4-(3-chlorophenoxy)phenoxymethyl]-2-propyl-1,3-dioxolane;

4-[2-chloro-4-(3-chlorophenoxy)phenoxymethyl]-2-isopropyl-1,3-dioxolane;

4-[2-chloro-4-(3,5-difluorophenoxy)phenoxymethyl]-2-ethyl-1,3-dioxolane;

4-[2-chloro-4-(3,5-difluorophenoxy)phenoxymethyl]-2-propyl-1,3-dioxolane;

4-[2-chloro-4-(3,5-difluorophenoxy)phenoxymethyl]-2-isopropyl-1,3-dioxolane;

4-[2-chloro-4-(3,4-dichlorophenoxy)phenoxymethyl]-2-ethyl-1,3-dioxolane;

4-[2-chloro-4-(3-chloro-4-fluorophenoxy)phenoxymethyl]-2-ethyl-1,3-dioxolane;

4-(2-chloro-4-benzylphenoxymethyl)-2-ethyl-1,3-dioxolane;

4-(2-chloro-4-benzylphenoxymethyl)-2-propyl-1,3-dioxolane;

4-(2-chloro-4-benzylphenoxymethyl)-2-isopropyl-1,3-dioxolane;

4-(2-chloro-4-benzylphenoxymethyl)-2-cyclopropyl-1,3-dioxolane;

4-[2-chloro-4-(3-fluorobenzyl)phenoxymethyl]-2-ethyl-1,3-dioxolane;

4-[2-chloro-4-(3-fluorobenzyl)phenoxymethyl]-2-propyl-1,3-dioxolane;

4-[2-chloro-4-(3,5-difluorobenzyl)phenoxymethyl]-2-ethyl-1,3-dioxolane and

4-[2-chloro-4-(3,4-dichlorobenzyl)phenoxymethyl]-2-ethyl-1,3-dioxolane.

The invention also relates to the process for the preparation of the compounds of the formula I which comprises, for example, a) reacting a compound of the formula

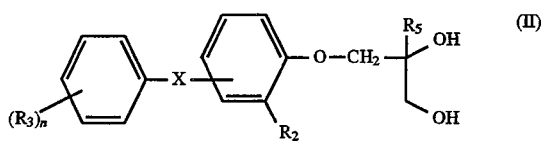

with a compound of the formula

preferably in the presence of an acidic catalyst, or b) reacting a compound of the formula

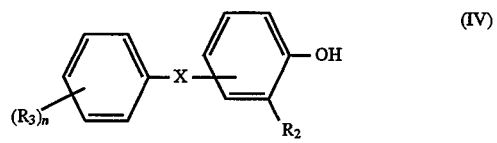

with a compound of the formula

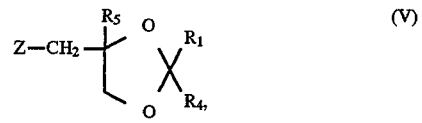

preferably in the presence of a base, or c) reacting a compound of the formula II with a compound of the formula

preferably in the presence of an acidic catalyst, where n, $R_1$, $R_2$, $R_3$, $R_4$, $R_5$ and X are in each case as defined for formula I, $R_6$ and $R_7$ either independently of one another are $C_1$–$C_8$alkyl or together are —$(CH_2)_2$— or —$(CH_2)_3$— and Z is chlorine, bromine, iodine, methanesulfonyloxy or p-toluenesulfonyloxy and, if desired, in each case a mixture of isomers which can be obtained according to the process is separated and the desired isomer is isolated.

The reactions described hereinbefore and hereinafter are carried out in a manner known per se, for example in the absence or, as a rule, in the presence of a suitable solvent or diluent or a mixture of these, the process being carried out, as required, with cooling, at room temperature or with heating, for example in a temperature range from approx. −80° C. to the boiling point of the reaction medium, preferably from approx. −20° C. to approx. +150° C., for example at the reflux temperature of the reaction mixture and, if necessary, in a sealed vessel, under pressure, in an inert gas atmosphere and/or under anhydrous conditions. Particularly advantageous reaction conditions can be seen from the examples. The starting material described hereinbefore and hereinafter, which is used for the preparation of the compounds I, is known or can be prepared by methods known per se, for example following the information given hereinafter.

Variant a):

Suitable acidic catalysts are, for example, sulfonic acids such as methane- or p-toluenesulfonic acid, including the acidic ion-exchanger resins having sulfo groups, Lewis acids such as boron trifluoride/diethyl ether complexes or boron trifluoride/dimethyl ether complexes, as well as mineral acids such as sulfuric acid or phosphoric acid.

The reactants can be reacted with each other as such, i.e. without an addition of a solvent or diluent, for example in the melt. However, in most cases it is advantageous to add an inert solvent or diluent or a mixture of these. Examples of such solvents or diluents which may be mentioned are: aromatic, aliphatic and alicyclic hydrocarbons and halohydrocarbons such as benzene, toluene, xylene, chlorobenzene, bromobenzene, petroleum ether, hexane, cyclohexane, dichloromethane, trichloromethane, dichloroethane or trichloroethene; ethers such as diethyl ether, tert-butyl methyl ether, tetrahydrofuran or dioxane; ketones such as acetone or methyl ethyl ketone; amides such as N,N-dimethylformamide, N,N-dimethylacetamide, N-methylpyrrolidone or hexamethylphosphoric triamide; nitriles such as acetonitrile; and sulfoxides such as dimethyl sulfoxide.

The reaction is carried out advantageously in a temperature range from approx. 0° C. to approx. +180° C., preferably from approx. +20° C. to approx. ⊕130° C., in many cases at the reflux temperature of the solvent used.

In a preferred embodiment of variant a), a compound II is reacted with a compound III at reflux temperature, in an aromatic hydrocarbon, preferably in toluene, and in the presence of a sulfonic acid as catalyst, preferably in the presence of p-toluenesulfonic acid.

The compounds II are known or can be prepared in analogy to known compounds, for example by reacting a compound of the formula IV with 2-$R_5$-2,3-epoxypropan-1-ol, the process being carried out in a manner known per se, advantageously in an inert solvent or diluent, for example of the abovementioned type, for example in an aromatic hydrocarbon such as toluene or xylene, in the presence of a catalyst, for example a quaternary ammonium salt, such as in the presence of tetramethylammonium chloride, and at room temperature or increased temperature, for example in a temperature range from approx. 20° C. to approx. 200° C., preferably from approx. 50° C. to approx. 150° C.

The compounds of the formula III are known or can be prepared in analogy to known compounds.

The compounds IV are known or can be prepared in analogy to known compounds.

Variant b):

Bases which are suitable for facilitating the elimination of HZ are, for example, hydroxides, hydrides, amides, alkanolates, carbonates, dialkylamides or alkylsilylamides of alkali metals or alkaline earth metals, or alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine; 4-(N,N-dimethylamino)pyridine, N-methylmorpholine, benzyltrimethylammonium hydroxide as well as 1,5-diazabicyclo[5.4.0]undec-5-ene(DBU).

The reaction is carried out advantageously in an inert solvent or diluent, for example of the type mentioned under variant a), and in a temperature range from approx. −80° C. to approx. +200° C., for example from approx. −20° C. to approx. +100° C.

The compounds of the formula V are known or can be prepared in analogy to known compounds.

Variant c):

Suitable acidic catalysts are, for example, of the type mentioned under variant a) for the reaction of compounds II and III.

The reaction is carried out advantageously in an inert solvent or diluent, for example of the type mentioned under variant a), and in a temperature range from approx. 0° C. to approx. +180° C., preferably from approx. +20° C. to approx. +130° C., frequently at the reflux temperature of the solvent used.

The compounds of the formula VI are known or can be prepared in analogy to known compounds.

The compounds I can exist in the form of one of the possible isomers or as a mixture of these, for example as pure isomers, such as antipodes and/or diastereomers, or as isomer mixtures, such as enantiomer mixtures, for example racemates, diastereomer mixtures or racemate mixtures, depending on the number and the absolute and relative configuration of the asymmetric carbon atoms; the invention relates to the pure isomers and to all possible isomer mixtures and is to be understood correspondingly in each case hereinbefore and hereinafter even when stereochemical details are not mentioned specifically in each case.

Diastereomer mixtures and racemate mixtures of compounds I which can be obtained according to the process—depending on the choice of starting materials and the procedures—or by other routes can be resolved in a known manner on the basis of the physicochemical differences of the components to give the pure diastereomers or racemates, for example by fractional crystallisation, distillation and/or chromatography.

Enantiomer mixtures which can be obtained accordingly, such as racemates, can be resolved by known methods to give the optical antipodes, for example by recrystallisation from an optically active solvent, by chromatography on chiral adsorbents, for example high-pressure liquid chromatography (HPLC) on acetylcellulose, with the aid of suitable microorganisms, by cleavage with specific, immobilised enzymes, via the formation of inclusion compounds, for example using chiral crown ethers, where only one enantiomer is complexed.

Pure diastereomers or enantiomers can be obtained according to the invention not only by separating corresponding isomer mixtures but also by generally known methods of diastereoselective or enantioselective synthesis, for example by carrying out the process according to the invention with educts whose stereochemistry is suitable.

It is advantageous to isolate or synthesise in each case the biologically more active isomer, for example enantiomer, or isomer mixture, for example enantiomer mixture, if the individual components differ in their biological activity.

The compounds I can also be obtained in the form of their hydrates and/or include other solvents, for example those which may have been used for the crystallisation of compounds in solid form.

The invention relates to all those embodiments of the process which start from a compound which can be obtained in any desired step of the process as starting material or intermediate and in which all or some of the missing steps are carried out, or in which a starting material in the form of a derivative or salt and/or racemates or antipodes thereof are used or, in particular, formed under the reaction conditions.

The process of the present invention preferably uses those starting materials and intermediates which lead to the compounds I which have been described at the outset as being particularly valuable.

In particular, the invention relates to the preparation processes described in Examples H1 to H5.

The invention also relates to starting materials and intermediates which are used according to the invention for the preparation of the compounds I and which are novel, and to their use and to processes for their preparation.

In this context, the compounds II, which are also part of the present invention, and their preparation and their use as intermediates are of particular importance.

Dioxolanes which are substituted in the 4-position and which have a similar structure have already been disclosed, for example in the European patent application with the Publication Number 0 411 676. The compounds I of the present invention differ from these known compounds in structural terms in a characteristic manner in that they are substituted in the 2-position of the phenyl ring of the phenoxymethyl group shown in formula I by $C_1$–$C_3$alkyl, halo-$C_1$–$C_3$alkyl, $C_1$–$C_3$alkoxy, halo-$C_1$–$C_3$alkoxy, fluorine, chlorine or bromine ($R_2$); moreover, the compounds I of the present invention have an activity in the field of pest control which is increased to a surprising extent.

The compounds I of the present invention are oils, resins or solids which are stable at room temperature. While having a favourable tolerability for warm-blooded species, fish and plants, they are valuable active ingredients in the field of pest control. The active ingredients according to the invention are particularly active against insects and arachnids, as they can be found on useful plants and ornamentals in agriculture and horticulture, in particular in rice, cotton, vegetable and fruit crops, and in forests. The compounds I are particularly suitable for controlling insects in crops of rice, fruit and vegetables, in particular for controlling plant-injurious insects such as *Nilaparvata lugens* and *Heliothis virescens*. Other fields in which the active ingredients according to the invention can be applied are the protection of stored goods and of materials, and in the hygiene sector, in particular the protection of domestic animals and productive livestock. The compounds I are active against all or individual development stages of normally-sensitive, but also resistant pests species. Their action may become apparent for example by destruction of the pests, either immediately or only after some time has elapsed, for example during moulting, or by reduced oviposition and/or hatching rate.

The abovementioned pests include:

from the order of the Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order of the Coleoptera, for example Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order of the Orthoptera, for example Blatta spp., Blattella spp., Gryllotalpa spp., *Leucophaea maderae*, Locusta spp., Periplaneta spp. and Schistocerca spp.;

from the order of the Isoptera, for example Reticulitermes spp.;

from the order of the Psocoptera, for example Liposcelis spp.;

from the order of the Anoplura, for example Haematopinus spp., Linognathus spp., Pediculus spp., Pemphigus spp. and Phylloxera spp.;

from the order of the Mallophaga, for example Damalinea spp. and Trichodectes spp.;

from the order of the Thysanoptera, for example Frankliniella spp., Hercinothrips spp., Taeniothrips spp., *Thrips palmi, Thrips tabaci* and *Scirtothrips aurantii;* from the order of the Heteroptera, for example Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

from the order of the Homoptera, for example *Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri*;

from the order of the Hymenoptera, for example Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

from the order of the Diptera, for example Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, *Pegomyia hyoscyami*, Phorbia spp., *Rhagoletis pomonella*, Sciara spp., Stomoxys spp., Tabanus spp., Tannia spp. and Tipula spp.;

from the order of the Siphonaptera, for example Ceratophyllus spp. and *Xenopsylla cheopis;* from the order of the Thysanura, for example *Lepisma saccharina* and from the order of the Acarina, for example *Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp. and Tetranychus spp.

The good pesticidal activity of the compounds I according to the invention is reflected in a destruction rate (mortality) of at least 50–60% of the abovementioned pests.

The activity of the compounds I according to the invention and the compositions comprising them can be broadened substantially and adapted to prevailing circumstances by adding other insecticides and/or acaricides. Suitable additions are, for example, representatives of the following classes of active ingredients: organophosphorus compounds, nitrophenols and derivatives, formamidines, ureas, carbamates, pyrethroids, chlorinated hydrocarbons and *Bacillus thuringiensis* preparations.

The compounds I are employed as pure active ingredients or, preferably, together with the auxiliaries conventionally used in the art of formulation, and they can therefore be processed in a known manner to give, for example, emulsifiable concentrates, directly sprayable or dilutable solutions, dilute emulsions, wettable powders, soluble powders, dusts and granules, and also encapsulations in polymeric substances. The application methods such as spraying, atomising, dusting, scattering or pouring, as well as the compositions are selected to suit the intended aims and the prevailing circumstances. The compounds I are furthermore suitable for use in the treatment of seed. The seed can be treated or dressed with the active ingredient, or a formulation comprising the active ingredient, before sowing, or the active ingredient can be applied to the seed furrow during sowing:

The formulations, i.e. the compositions, preparations or combinations comprising the active ingredient of the formula I, or a combination of this active ingredient with other insecticides and/or acaricides, and, if desired, solid or liquid adjuvants, are prepared in a known manner, for example by intimately mixing and/or grinding the active ingredient with the adjuvants such as extenders, for example solvents or solid carriers, or such as surface-active compounds (surfactants).

The following are suitable as solvents: aromatic hydrocarbons, preferably the fractions $C_8$ to $C_{12}$ of alkylbenzenes such as xylene mixtures or alkylated naphthalenes, aliphatic or cycloaliphatic hydrocarbons such as cyclohexane, paraffins or tetrahydronaphthalene, alcohols such as ethanol, propanol or butanol, glycols as well as their ethers and esters such as propylene glycol, dipropylene glycol ether, ethylene glycol, ethylene glycol monomethyl ether or ethylene glycol monoethyl ether, ketones such as cyclohexanone, isophorone or diacetone alcohol, strongly polar solvents such as N-methyl-2-pyrrolidone, dimethyl sulfoxide or N,N-dimethylformamide, water and epoxidised or unepoxidised vegetable oils such as epoxidised or unepoxidised rapeseed oil, castor oil, coconut oil or soya oil; silicone oils may also be used.

Solid carriers which are suitable, for example for dusts and dispersible powders, are, as a rule, ground natural minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types such as pumice, crushed brick, sepiolite or bentonite, or non-sorptive carrier materials, such as calcite or sand. Moreover, a large number of granulated materials of inorganic or organic nature can be used, in particular dolomite or comminuted plant residues.

Suitable surface-active compounds are non-ionic, cationic and/or anionic surfactants which have good emulsifying, dispersing and wetting properties, depending on the nature of the active ingredient I to be formulated or of the combination of this active ingredient with other insecticides and/or acaricides. Surfactants are also to be understood as meaning mixtures of surfactants.

Suitable non-ionic surfactants are mainly polyglycol ether derivatives of aliphatic or cycloaliphatic alcohols, saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols. Also suitable are the water-soluble polyethylene oxide adducts with polypropylene glycol, ethylenediaminopolypropylene glycol and alkyl polypropylene glycol which have 1 to 10 carbon atoms in the alkyl chain and contain 20 to 250 ethylene glycol ether groups and 10 to 100 propylene glycol ether groups. As a rule, the compounds mentioned contain 1 to 5 ethylene glycol units per propylene glycol unit. Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Other suitable substances are fatty acid esters of polyoxyethylene sorbitan, such as polyoxyethylene sorbitan trioleate.

The cationic surfactants are mainly quaternary ammonium salts which contain at least one alkyl radical having 8 to 22 C atoms as N substituents and which have lower halogenated or free alkyl, benzyl or lower hydroxyalkyl radicals as further substituents. The salts are preferably in the form of halides, methyl sulfates or ethyl sulfates, for example stearyltrimethylammonium chloride or benzyldi(2-chloroethyl)ethylammonium bromide.

Suitable anionic surfactants can be either so-called water-soluble soaps or water-soluble synthetic surface-active compounds. Soaps which are suitable are the alkali metal salts, alkaline earth metal salts or substituted or unsubstituted ammonium salts of higher fatty acids ($C_{10}$–$C_{22}$) such as the sodium salts or potassium salts of oleic or stearic acid, or of natural mixtures of fatty acids which can be obtained, for example, from coconut oil or tall oil; mention must also be made of the fatty acid methyltaurinates. However, so-called synthetic surfactants are used more frequently, in particular fatty sulfonates, fatty sulfates, sulfonated benzimidazole derivatives or alkylarylsulfonates. The fatty sulfonates or fatty sulfates are, as a rule, in the form of alkali metal salts, alkaline earth metal salts or substituted or unsubstituted ammonium salts and have, as a rule, an alkyl radical having 8 to 22 C atoms, alkyl also including the alkyl moiety of acyl radicals; examples which may be mentioned are the sodium salt or calcium salt of ligninsulfonic acid, of dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfo groups and a fatty acid radical having approx. 8–22 C atoms. Examples of alkylarylsulfonates are the sodium, calcium or triethanolammonium salts of dodecylbenzenesulfonic acid, of dibutylnaphthalenesulfonic acid or of a naphthalenesulfonic acid/formaldehyde condensation product. Other suitable compounds are the corresponding phosphates, such as salts of the phosphoric ester of a p-nonylphenol/(4–14)-ethylene oxide adduct, or phospholipids.

The abovementioned surfactants are only to be understood as being examples; a large number of further surfactants which are conventionally used in the art of formulation and which are suitable according to the invention are described in the specialist literature.

As a rule, the pesticidal compositions comprise 0.1 to 99%, in particular 0.1 to 95%, of active ingredient I or of the combination of this active ingredient with other insecticides and/or acaricides and 1 to 99.9%, in particular 5 to 99.9%, of a solid or liquid adjuvant, and, as a rule, 0 to 25%, in particular 0.1 to 20% of the preparations can be composed of surfactants (%= is in each case to be understood as meaning percent by weight). While concentrated compositions are more preferred as commercial goods, the end user usually uses dilute compositions with much lower concentrations of active ingredient. Typical use concentrations are between 0.1 and 1000 ppm, preferably between 0.1 and 500 ppm. As a rule, the application rates per hectare are 1 to 1000 g of active ingredient per hectare, preferably 25 to 500 g/ha.

Preferred formulations have, in particular, the following composition (%=percent by weight):

Emulsifiable concentrates:

Active ingredient: 1 to 90%, preferably 5 to 20%

Surfactant: 1 to 30%, preferably 10 to 20%

Liquid carrier: 5 to 94%, preferably 70 to 85%

Dusts:

Active ingredient: 0.1 to 10%, preferably 0.1 to 1%

Solid carrier: 99.9 to 90%, preferably 99.9 to 99%

Suspension concentrates:

Active ingredient: 5 to 75%, preferably 10 to 50%

Water: 94 to 24%, preferably 88 to 30%

Surfactant: 1 to 40%, preferably 2 to 30%

Wettable powders:

Active ingredient: 0.5 to 90%, preferably 1 to 80%

Surfactant: 0.5 to 20%, preferably 1 to 15%

Solid carrier: 5 to 95%, preferably 15 to 90%

Granules:

Active ingredient: 0.5 to 30%, preferably 3 to 15%

Solid carrier: 99.5 to 70%, preferably 97 to 85%

The preparations can also comprise further adjuvants such as stabilisers, for example epoxidised or unepoxidised vegetable oils (for example epoxidised coconut oil, rapeseed oil or soya oil), defoamers, for example silicone oil, preservatives, viscosity regulators, binders and/or tackifiers, as well as fertilisers or other active ingredients for achieving specific effects.

The invention also embraces a method of controlling the abovementioned pests, which is distinguished by applying an active ingredient of the formula I, or a composition according to the invention which comprises an active ingredient of the formula I, to the pests or the various development stages of the pests, or to their locus.

The examples which follow illustrate the above-described invention without imposing any limitation to its scope. "$n_D^{T°}$" is the refractive index at a temperature of T° C. Temperatures are given in degrees Celsius. "m.p." is the melting point; "%" is percent by weight, unless otherwise indicated. Compounds I in which $R_1$ and $R_4$ are different can form diastereomers; "A" and "B" are in each case the two separated diastereomer components of such mixtures; if, however, no symbols "A" and "B" are given, the product is a diastereomer mixture.

PREPARATION EXAMPLES

EXAMPLE H1

3-(2-Chloro-4-phenoxyphenoxy)-1,2-dihydroxypropane

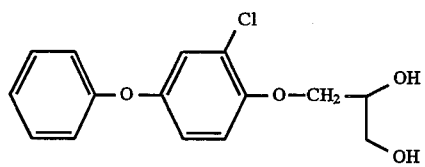

0.2 g of tetramethylammonium chloride is added to a solution of 22.1 g (0.1 mol) of 2-chloro-4-phenoxyphenol in 20 ml of xylene, the mixture is heated at 60° C., and 8.1 g of 2,3-epoxypropan-1-ol are added dropwise with stirring in the course of 20 minutes. Stirring of the reaction mixture is then continued for 8 hours at 90° C., 60 ml of hexane are added with stirring at 60° C. in the course of 5 minutes, the mixture is cooled to 0° C., and the solid which has precipitated is filtered off. The crude product obtained is recrystallised in isopropanol/hexane. Colourless crystals of the title compound with a melting point of 87°–88° C. (Compound No. 1.13) are obtained.

EXAMPLE H2

The other compounds of the formula II which are listed in Table 1 can also be prepared analogously to the procedure given in Example H1, if desired after additional purification by chromatography [$CH_2Cl_2/(C_2H_5)_2O=3:2$].

TABLE 1

| Comp. No. | $R_2$ | $(R_3)_n$ | X | Physical Data |
|---|---|---|---|---|
| 1.1 | Cl | 3-F | O | $n_D^{20}$ = 1.5782 |
| 1.2 | Cl | 3-Cl | O | $n_D^{20}$ = 1.5940 |
| 1.3 | Cl | 3-F,5-F | O | m.p. = 52–53° |
| 1.4 | Cl | 3-Cl,4-F | O | $n_D^{20}$ = 1.5706 |
| 1.5 | Cl | 3-Cl,4-Cl | O | m.p. = 61–62° |
| 1.6 | Cl | 3-Cl,5-Cl | O | |
| 1.7 | Cl | 4-F | O | $n_D^{20}$ = 1.5762 |
| 1.8 | Cl | 4-Cl | O | $n_D^{20}$ = 1.5920 |
| 1.9 | Cl | 3-CH$_3$ | O | $n_D^{20}$ = 1.5671 |
| 1.10 | Cl | 2-F,4-F | O | |
| 1.11 | CH$_3$ | n = 0 | O | $n_D^{20}$ = 1.5724 |
| 1.12 | CH$_3$ | 3-F | O | $n_D^{20}$ = 1.5621 |
| 1.13 | Cl | n = 0 | O | m.p. = 87–88° |
| 1.14 | CH$_3$ | 3-F,5-F | O | $n_D^{20}$ = 1.5702 |
| 1.15 | CH$_3$ | 3-Cl | O | $n_D^{20}$ = 1.5794 |
| 1.16 | CH$_3$ | 3-Cl,4-Cl | O | m.p. = 42–43° |
| 1.17 | CH$_3$ | 3-Cl,4-F | O | |
| 1.18 | Cl | n = 0 | CH$_2$ | m.p. = 75–77° |
| 1.19 | CH$_3$ | n = 0 | CH$_2$ | m.p. = 73–74° |
| 1.20 | Cl | 3-F | CH$_2$ | m.p. = 80–81° |
| 1.21 | CH$_3$ | 3-F | CH$_3$ | $n_D^{20}$ = 1.5621 |
| 1.22 | Cl | 3-F,5-F | CH$_2$ | m.p. = 89–90° |
| 1.23 | Cl | 3-Cl,4-Cl | CH$_2$ | m.p. = 97–98° |
| 1.24 | Br | n = 0 | O | m.p. =79–80° |
| 1.25 | Br | 3-F | O | $n_D^{20}$ = 1.5869° |
| 1.26 | Br | n = 0 | CH$_2$ | m.p. = 89–90° |
| 1.27 | Cl | n = 0 | C=O | $n_D^{20}$ = 1.6139 |
| 1.28 | Cl | 4-Cl | C=O | m.p. = 112–113° |
| 1.29 | F | n = 0 | O | m.p. = 74–75° |
| 1.30 | F | 3-Cl | O | $n_D^{20}$ = 1.5671 |
| 1.31 | F | 3-F | O | $n_D^{20}$ = 1.5529 |
| 1.32 | Br | 3-Cl,4-Cl | CH$_2$ | |
| 1.33 | F | 3-F | CH$_2$ | |

EXAMPLE H3

4-(2-Chloro-4-phenoxyphenoxymethyl)-2-ethyl-1,3-dioxolane

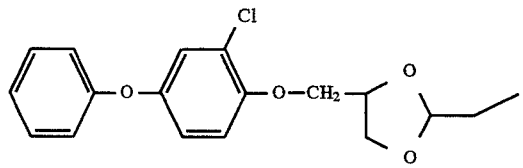

1.6 g (0.028 mol) of freshly distilled propanal are added dropwise with stirring at reflux temperature to a solution of 5.9 g (0.02 mol) of 3-(2-chloro-4-phenoxyphenoxy)-1,2-dihydroxypropane and 20 mg of 4-toluenesulfonic acid in 40 ml of toluene. Stirring of the mixture is continued for 6 hours at reflux temperature, and the mixture is then washed repeatedly with 10% sodium carbonate solution and then with water. The toluene phase is dried over sodium sulfate and freed from solvent in vacuo. Chromatographic purification of the crude product on silica gel [hexane:diethyl ether (15: 1)] gives the title compound in the form of two separate diastereomers [diastereomer A (Compound No. 2.3.1): $n_D^{20}$=1.5591; diastereomer B (Compound No. 2.3.2): $n_D^{20}$=1.5611].

EXAMPLE H4

The other compounds of the formula I which are listed in Tables 2 to 8 can also be prepared analogously to the procedure given in Example H3.

TABLE 2

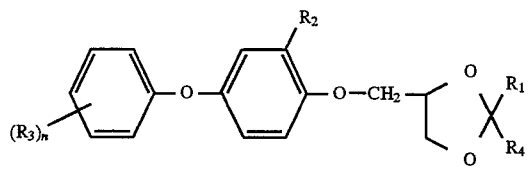

| Comp. No. | $R_1$ | $R_2$ | $(R_3)_n$ | $R_4$ | Physical Data |
|---|---|---|---|---|---|
| 2.1 | $CH_3$ | Cl | n = 0 | $CH_3$ | $n_D^{20}$ = 1.5564 |
| 2.2 | $CH_3$ | Cl | n = 0 | H | |
| 2.3 | $C_2H_5$ | Cl | n = 0 | H | |
| 2.3.1 | $C_2H_5$ | Cl | n = 0 | H | A; $n_D^{20}$ = 1.5591 |
| 2.3.2 | $C_2H_5$ | Cl | n = 0 | H | B; $n_D^{20}$ = 1.5611 |
| 2.4 | $C_3H_7$ | Cl | n = 0 | H | |
| 2.4.1 | $C_3H_7$ | Cl | n = 0 | H | A; $n_D^{20}$ = 1.5539 |
| 2.4.2 | $C_3H_7$ | Cl | n = 0 | H | B; $n_D^{20}$ = 1.5552 |
| 2.5 | i-$C_3H_7$ | Cl | n = 0 | H | $n_D^{20}$ = 1.5524 |
| 2.6 | i-$C_4H_9$ | Cl | n = 0 | H | |
| 2.7 | s-$C_4H_9$ | Cl | n = 0 | H | |
| 2.8 | cyclo-$C_3H_5$ | Cl | n = 0 | H | |
| 2.8.1 | cyclo-$C_3H_5$ | Cl | n = 0 | H | A; $n_D^{20}$ = 1.5693 |
| 2.8.2 | cyclo-$C_3H_5$ | Cl | n = 0 | H | B; $n_D^{20}$ = 1.5702 |
| 2.9 | $C_2H_5$ | $CH_3$ | n = 0 | H | |
| 2.9.1 | $C_2H_5$ | $CH_3$ | n = 0 | H | A; $n_D^{20}$ = 1.5463 |
| 2.9.2 | $C_2H_5$ | $CH_3$ | n = 0 | H | B; $n_D^{20}$ = 1.5481 |
| 2.10 | $C_3H_7$ | $CH_3$ | n = 0 | H | |
| 2.10.1 | $C_3H_7$ | $CH_3$ | n = 0 | H | A; $n_D^{20}$ = 1.5408 |
| 2.10.2 | $C_3H_7$ | $CH_3$ | n = 0 | H | B; $n_D^{20}$ = 1.5421 |
| 2.11 | i-$C_3H_7$ | $CH_3$ | n = 0 | H | |
| 2.12 | cyclo-$C_3H_5$ | $CH_3$ | n = 0 | $CH_3$ | |
| 2.13 | $CH_3$ | Cl | 3-F | $CH_3$ | |
| 2.14 | $CH_3$ | Cl | 3-F | H | |
| 2.14.1 | $CH_3$ | Cl | 3-F | H | A; $n_D^{20}$ = 1.5529 |
| 2.14.2 | $CH_3$ | Cl | 3-F | H | B; $n_D^{20}$ = 1.5541 |
| 2.15 | $C_2H_5$ | Cl | 3-F | H | |
| 2.15.1 | $C_2H_5$ | Cl | 3-F | H | A; $n_D^{20}$ = 1.5481 |
| 2.15.2 | $C_2H_5$ | Cl | 3-F | H | B; $n_D^{20}$ = 1.5501 |
| 2.16 | $C_3H_7$ | Cl | 3-F | H | |
| 2.16.1 | $C_3H_7$ | Cl | 3-F | H | A; $n_D^{20}$ = 1.5432 |
| 2.16.2 | $C_3H_7$ | Cl | 3-F | H | B; $n_D^{20}$ = 1.5456 |
| 2.17 | i-$C_3H_7$ | Cl | 3-F | H | |
| 2.17.1 | i-$C_3H_7$ | Cl | 3-F | H | A; $n_D^{20}$ = 1.5422 |
| 2.17.2 | i-$C_3H_7$ | Cl | 3-F | H | B; $n_D^{20}$ = 1.5431 |
| 2.18 | s-$C_4H_9$ | Cl | 3-F | H | |
| 2.19 | i-$C_4H_9$ | Cl | 3-F | H | |
| 2.19.1 | i-$C_4H_9$ | Cl | 3-F | H | A; $n_D^{20}$ = 1.5382 |
| 2.19.2 | i-$C_4H_9$ | Cl | 3-F | H | B; $n_D^{20}$ = 1.5392 |
| 2.20 | cyclo-$C_3H_5$ | Cl | 3-F | H | |
| 2.20.1 | cyclo-$C_3H_5$ | Cl | 3-F | H | A; $n_D^{20}$ = 1.5592 |
| 2.20.2 | cyclo-$C_3H_5$ | Cl | 3-F | H | B; $n_D^{20}$ = 1.5612 |
| 2.21 | $C_2H_5$ | $CH_3$ | 3-F | H | $n_D^{20}$ = 1.5371 |
| 2.22 | $C_3H_7$ | $CH_3$ | 3-F | H | $n_D^{20}$ = 1.5332 |
| 2.23 | i-$C_3H_7$ | $CH_3$ | 3-F | H | |
| 2.24 | $CH_3$ | Cl | 3-F,5-F | $CH_3$ | |
| 2.25 | $CH_3$ | Cl | 3-F,5-F | H | |
| 2.26 | $C_2H_5$ | Cl | 3-F,5-F | H | |

TABLE 2-continued

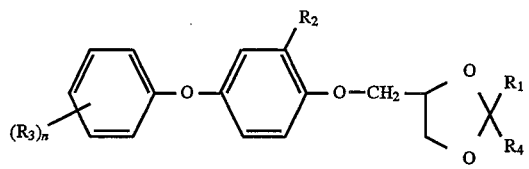

| Comp. No. | $R_1$ | $R_2$ | $(R_3)_n$ | $R_4$ | Physical Data |
|---|---|---|---|---|---|
| 2.26.1 | $C_2H_5$ | Cl | 3-F,5-F | H | A; $n_D^{20}$ = 1.5369 |
| 2.26.2 | $C_2H_5$ | Cl | 3-F,5-F | H | B; $n_D^{20}$ = 1.5379 |
| 2.27 | $C_3H_7$ | Cl | 3-F,5-F | H | |
| 2.27.1 | $C_3H_7$ | Cl | 3-F,5-F | H | A; $n_D^{20}$ = 1.5330 |
| 2.27.2 | $C_3H_7$ | Cl | 3-F,5-F | H | B; $n_D^{20}$ = 1.5339 |
| 2.28 | i-$C_3H_7$ | Cl | 3-F,5-F | H | |
| 2.28.1 | i-$C_3H_7$ | Cl | 3-F,5-F | H | A; $n_D^{20}$ = 1.5325 |
| 2.28.2 | i-$C_3H_7$ | Cl | 3-F,5-F | H | B; $n_D^{20}$ = 1.5331 |
| 2.29 | i-$C_4H_9$ | Cl | 3-F,5-F | H | |
| 2.30 | $C_4H_9$ | Cl | 3-F,5-F | H | |
| 2.31 | s-$C_4H_9$ | Cl | 3-F,5-F | H | |
| 2.32 | cyclo-$C_3H_5$ | Cl | 3-F,5-F | H | |
| 2.32.1 | cyclo-$C_3H_5$ | Cl | 3-F,5-F | H | A; $n_D^{20}$ = 1.5461 |
| 2.32.2 | cyclo-$C_3H_5$ | Cl | 3-F,5-F | H | B; $n_D^{20}$ = 1.5470 |
| 2.33 | $C_2H_5$ | $CH_3$ | 3-F,5-F | H | |
| 2.34 | $C_3H_7$ | $CH_3$ | 3-F,5-F | H | |
| 2.35 | i-$C_3H_7$ | $CH_3$ | 3-F,5-F | H | |
| 2.36 | cyclo-$C_3H_5$ | $CH_3$ | 3-F,5-F | $CH_3$ | |
| 2.37 | $CH_3$ | Cl | 3-Cl | $CH_3$ | |
| 2.38 | $C_2H_5$ | Cl | 3-Cl | H | |
| 2.38.1 | $C_2H_5$ | Cl | 3-Cl | H | A; $n_D^{20}$ = 1.5662 |
| 2.38.2 | $C_2H_5$ | Cl | 3-Cl | H | B; $n_D^{20}$ = 1.5679 |
| 2.39 | $C_3H_7$ | Cl | 3-Cl | H | |
| 2.39.1 | $C_3H_7$ | Cl | 3-Cl | H | A; $n_D^{20}$ = 1.5604 |
| 2.39.2 | $C_3H_7$ | Cl | 3-Cl | H | B; $n_D^{20}$ = 1.5624 |
| 2.40 | i-$C_3H_7$ | Cl | 3-Cl | H | |
| 2.41 | cyclo-$C_3H_5$ | Cl | 3-Cl | H | |
| 2.42 | $C_2H_5$ | $CH_3$ | 3-Cl | H | $n_D^{20}$ = 1.5561 |
| 2.43 | $CH_3$ | Cl | 4-F | $CH_3$ | |
| 2.44 | $C_2H_5$ | Cl | 4-F | H | |
| 2.45 | $C_3H_7$ | Cl | 4-F | H | |
| 2.46 | i-$C_3H_7$ | Cl | 4-F | H | |
| 2.47 | cyclo-$C_3H_5$ | Cl | 4-F | H | |
| 2.48 | $CH_3$ | Cl | 4-Cl | H | |
| 2.49 | $C_2H_5$ | Cl | 4-Cl | H | |
| 2.50 | $C_3H_7$ | Cl | 4-Cl | H | |
| 2.51 | i-$C_3H_7$ | Cl | 4-Cl | H | |
| 2.52 | cyclo-$C_3H_5$ | Cl | 4-Cl | H | |
| 2.53 | $CH_3$ | Cl | 3-$CH_3$ | $CH_3$ | |
| 2.54 | $CH_3$ | Cl | 3-$CH_3$ | H | |
| 2.55 | $C_2H_5$ | Cl | 3-$CH_3$ | H | |
| 2.56 | $C_3H_7$ | Cl | 3-$CH_3$ | H | |
| 2.57 | i-$C_3H_7$ | Cl | 3-$CH_3$ | H | |
| 2.58 | cyclo-$C_3H_5$ | Cl | 3-$CH_3$ | H | |
| 2.59 | $CH_3$ | Cl | 3-Cl,4-Cl | $CH_3$ | |
| 2.60 | $CH_3$ | Cl | 3-Cl,4-Cl | H | |
| 2.61 | $C_2H_5$ | Cl | 3-Cl,4-Cl | H | |
| 2.61.1 | $C_2H_5$ | Cl | 3-Cl,4-Cl | H | A; $n_D^{20}$ = 1.5749 |
| 2.61.2 | $C_2H_5$ | Cl | 3-Cl,4-Cl | H | B; $n_D^{20}$ = 1.5758 |
| 2.62 | $C_3H_7$ | Cl | 3-Cl,4-Cl | H | |
| 2.62.1 | $C_3H_7$ | Cl | 3-Cl,4-Cl | H | A; $n_D^{20}$ = 1.5691 |
| 2.62.2 | $C_3H_7$ | Cl | 3-Cl,4-Cl | H | B; $n_D^{20}$ = 1.5705 |
| 2.63 | i-$C_3H_7$ | Cl | 3-Cl,4-Cl | H | |
| 2.64 | i-$C_4H_9$ | Cl | 3-Cl,4-Cl | H | |
| 2.65 | cyclo-$C_3H_5$ | Cl | 3-Cl,4-Cl | H | |
| 2.65.1 | cyclo-$C_3H_5$ | Cl | 3-Cl,4-Cl | H | A; $n_D^{20}$ = 1.5798 |
| 2.65.2 | cyclo-$C_3H_5$ | Cl | 3-Cl,4-Cl | H | B; $n_D^{20}$ = 1.5815 |
| 2.66 | cyclo-$C_3H_5$ | Cl | 3-Cl,4-Cl | $CH_3$ | |
| 2.67 | $C_2H_5$ | $CH_3$ | 3-Cl,4-Cl | H | |
| 2.68 | $C_3H_7$ | $CH_3$ | 3-Cl,4-Cl | H | |
| 2.69 | $CH_3$ | Cl | 3-Cl,4-F | $CH_3$ | |
| 2.70 | $CH_3$ | Cl | 3-Cl,4-F | H | |
| 2.71 | $C_2H_5$ | Cl | 3-Cl,4-F | H | |
| 2.71.1 | $C_2H_5$ | Cl | 3-Cl,4-F | H | A; $n_D^{20}$ = 1.5561 |
| 2.71.2 | $C_2H_5$ | Cl | 3-Cl,4-F | H | B; $n_D^{20}$ = 1.5572 |
| 2.72 | $C_3H_7$ | Cl | 3-Cl,4-F | H | |
| 2.73 | i-$C_3H_7$ | Cl | 3-Cl,4-F | H | |
| 2.74 | cyclo-$C_3H_5$ | Cl | 3-Cl,4-F | H | |

TABLE 2-continued

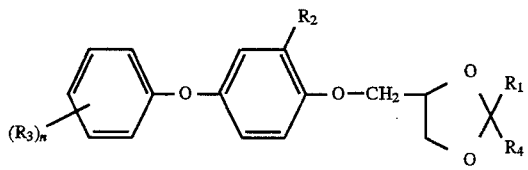

| Comp. No. | $R_1$ | $R_2$ | $(R_3)_n$ | $R_4$ | Physical Data |
|---|---|---|---|---|---|
| 2.75 | cyclo-$C_3H_5$ | Cl | 3-Cl,4-F | $CH_3$ | |
| 2.76 | $C_2H_5$ | $CH_3$ | 3-Cl,4-F | H | |
| 2.77 | $CH_3$ | Cl | 2-F,4-F | $CH_3$ | |
| 2.78 | $CH_3$ | Cl | 2-F,4-F | H | |
| 2.79 | $C_2H_5$ | Cl | 2-F,4-F | H | |
| 2.80 | $C_3H_7$ | Cl | 2-F,4-F | H | |
| 2.81 | i-$C_3H_7$ | Cl | 2-F,4-F | H | |
| 2.82 | cyclo-$C_3H_5$ | Cl | 2-F,4-F | H | |
| 2.83 | i-$C_4H_9$ | Cl | 3-Cl | H | |
| 2.83.1 | i-$C_4H_9$ | Cl | 3-Cl | H | A; $n_D^{20}$ = 1.5541 |
| 2.83.2 | i-$C_4H_9$ | Cl | 3-Cl | H | B; $n_D^{20}$ = 1.5552 |
| 2.84 | $C_2H_5$ | Br | H | H | |
| 2.84.1 | $C_2H_5$ | Br | H | H | A; $n_D^{20}$ = 1.5738 |
| 2.84.2 | $C_2H_5$ | Br | H | H | B; $n_D^{20}$ = 1.5754 |
| 2.85 | $R_1 + R_4$: $-(CH_2)_3-$ | Cl | 3-F | | $n_D^{20}$ = 1.5586 |
| 2.86 | $C_2H_5$ | Br | 3-F | H | |
| 2.86.1 | $C_2H_5$ | Br | 3-F | H | A; $n_D^{20}$ = 1.5584 |
| 2.86.2 | $C_2H_5$ | Br | 3-F | H | B; $n_D^{20}$ = 1.5611 |
| 2.87 | $C_3H_7$ | Br | 3-F | H | |
| 2.87.1 | $C_3H_7$ | Br | 3-F | H | A; $n_D^{20}$ = 1.5529 |
| 2.87.2 | $C_3H_7$ | Br | 3-F | H | B; $n_D^{20}$ = 1.5561 |
| 2.88 | $CH_3$ | Cl | 3-Cl | H | |
| 2.88.1 | $CH_3$ | Cl | 3-Cl | H | A; $n_D^{20}$ = 1.5701 |
| 2.88.2 | $CH_3$ | Cl | 3-Cl | H | B; $n_D^{20}$ = 1.5705 |
| 2.89 | $R_1 + R_4$: $-(CH_2)_5-$ | Cl | 3-Cl | | $n_D^{20}$ = 1.5631 |
| 2.90 | $R_1 + R_4$: $-(CH_2)_4-$ | Cl | 3-Cl | | $n_D^{20}$ = 1.5721 |
| 2.91 | $R_1 + R_4$: $-(CH_2)_4-$ | Cl | 3-F | | $n_D^{20}$ = 1.5539 |
| 2.92 | $R_1 + R_4$: $-(CH_2)_5-$ | Cl | 3-F | | $n_D^{20}$ = 1.5558 |
| 2.93 | $OCH_3$ | Cl | H | H | |
| 2.93.1 | $OCH_3$ | Cl | H | H | A; $n_D^{20}$ = 1.5646 |
| 2.93.2 | $OCH_3$ | Cl | H | H | B; $n_D^{20}$ = 1.5650 |
| 2.94 | $OCH_3$ | Cl | 3-Cl | H | |
| 2.94.1 | $OCH_3$ | Cl | 3-Cl | H | A; $n_D^{20}$ = 1.5700 |
| 2.94.2 | $OCH_3$ | Cl | 3-Cl | H | B; $n_D^{20}$ = 1.5706 |
| 2.95 | $OCH_3$ | Cl | 3-F | H | |
| 2.95.1 | $OCH_3$ | Cl | 3-F | H | A; $n_D^{20}$ = 1.5530 |
| 2.95.2 | $OCH_3$ | Cl | 3-F | H | B; $n_D^{20}$ = 1.5536 |
| 2.96 | $-CH=CH_2$ | Cl | 3-F | H | |
| 2.96.1 | $-CH=CH_2$ | Cl | 3-F | H | A; $n_D^{20}$ = 1.5572 |
| 2.96.2 | $-CH=CH_2$ | Cl | 3-F | H | B; $n_D^{20}$ = 1.5579 |
| 2.97 | $-CH=CH_2$ | Cl | H | H | |
| 2.97.1 | $-CH=CH_2$ | Cl | H | H | A; $n_D^{20}$ = 1.5681 |
| 2.97.2 | $-CH=CH_2$ | Cl | H | H | B; $n_D^{20}$ = 1.5698 |
| 2.98 | Ethynyl | Cl | 3-Cl | H | $n_D^{20}$ = 1.5798 |
| 2.99 | $C_3H_7$ | $CH_3$ | 3-Cl | H | $n_D^{20}$ = 1.5511 |
| 2.100 | $C_3H_7$ | F | H | H | |
| 2.100.1 | $C_3H_7$ | F | H | H | A; $n_D^{20}$ = 1.5355 |
| 2.100.2 | $C_3H_7$ | F | H | H | B; $n_D^{20}$ = 1.5369 |
| 2.101 | $C_2H_5$ | F | 3-Cl | H | |
| 2.101.1 | $C_2H_5$ | F | 3-Cl | H | A; $n_D^{20}$ = 1.5481 |
| 2.101.2 | $C_2H_5$ | F | 3-Cl | H | B; $n_D^{20}$ = 1.5491 |
| 2.102 | $C_3H_7$ | F | 3-Cl | H | |
| 2.102.1 | $C_3H_7$ | F | 3-Cl | H | A; $n_D^{20}$ = 1.5431 |
| 2.102.2 | $C_3H_7$ | F | 3-Cl | H | B; $n_D^{20}$ = 1.5448 |
| 2.103 | $C_2H_5$ | F | 3-F | H | |
| 2.103.1 | $C_2H_5$ | F | 3-F | H | A; $n_D^{20}$ = 1.5291 |
| 2.103.2 | $C_2H_5$ | F | 3-F | H | B; $n_D^{20}$ = 1.5306 |
| 2.104 | $C_3H_7$ | F | 3-F | H | |
| 2.104.1 | $C_3H_7$ | F | 3-F | H | A; $n_D^{20}$ = 1.5248 |
| 2.104.2 | $C_3H_7$ | F | 3-F | H | B; $n_D^{20}$ = 1.5262 |
| 2.105 | $C_6H_{13}$ | Cl | n = 0 | H | |
| 2.106 | $C_5H_{11}$ | Cl | 3-Cl | H | |
| 2.107 | s-$C_4H_9$ | Cl | 3-Cl | H | |
| 2.108 | $C_2H_5$ | Cl | 3-F | $CH_3$ | |
| 2.109 | cyclo-$C_3H_5$ | Cl | 3-Cl | $CH_3$ | |
| 2.110 | $C_2H_5$ | Cl | 3-Cl | $CH_3$ | |
| 2.111 | $-CH_2CH_2F$ | Cl | n = 0 | H | |
| 2.112 | $-CH_2CH_2F$ | Cl | 3-Cl | H | |

TABLE 2-continued

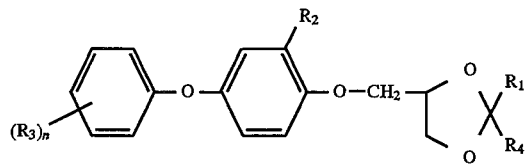

| Comp. No. | R₁ | R₂ | (R₃)ₙ | R₄ | Physical Data |
|---|---|---|---|---|---|
| 2.113 | —CH₂CH₂F | Cl | 3-F | H | |
| 2.114 | —CH₂CH₂F | Cl | 3-F,5-F | H | |
| 2.115 | —CH₂CH₂F | F | 3-F | H | |
| 2.116 | —CH₂CH₂F | CH₃ | 3-Cl | H | |
| 2.117 | —CH₂CH₂F | F | 3-Cl | H | |
| 2.118 | —CH₂CH₂F | F | n = 0 | H | |
| 2.119 | —CH₂CH₂Cl | Cl | n = 0 | H | |
| 2.120 | —CH₂CH₂Cl | Cl | 3-F | H | |
| 2.121 | —CH₂CH₂Cl | Cl | 3-Cl | H | |
| 2.122 | —CH=CH₂ | Cl | 3-Cl | H | |
| 2.123 | —CH=CH₂ | Cl | 3-F,5-F | H | |
| 2.124 | —CH=CHCH₃ (E) | Cl | 3-Cl | H | |
| 2.125 | —CH=CHCH₃ (Z) | Cl | 3-Cl | H | |
| 2.126 | —CH=CHCH₃ (E/Z) | F | 3-Cl | H | |
| 2.127 | —CH=C(CH₃)₂ | Cl | n = 0 | H | |
| 2.128 | —CH=C(CH₃)₂ | Cl | 3-Cl | H | |
| 2.129 | —CH=C(CH₃)₂ | Cl | 3-F | H | |
| 2.130 | i-C₄H₉ | F | n = 0 | H | |
| 2.131 | i-C₄H₉ | F | 3-Cl | H | |
| 2.132 | i-C₄H₉ | CH₃ | n = 0 | H | |
| 2.133 | i-C₄H₉ | CH₃ | 3-Cl | H | |
| 2.134 | i-C₄H₉ | CH₃ | 3-F | H | |
| 2.135 | —CHFCH₃ | Cl | n = 0 | H | |
| 2.136 | —CHFCH₃ | Cl | 3-Cl | H | |
| 2.137 | —CHFCH₃ | Cl | 3-F | H | |
| 2.138 | prop-1-yn-1-yl | Cl | n = 0 | H | |
| 2.139 | prop-1-yn-1-yl | Cl | 3-F | H | |
| 2.140 | prop-1-yn-1-yl | Cl | 3-Cl | H | |
| 2.141 | prop-1-yn-1-yl | CH₃ | n = 0 | H | |
| 2.142 | prop-1-yn-1-yl | CH₃ | 3-F | H | |
| 2.143 | but-1-yn-1-yl | Cl | n = 0 | H | |
| 2.144 | but-1-yn-1-yl | CH₃ | n = 0 | H | |
| 2.145 | but-1-yn-1-yl | F | 3-Cl | H | |
| 2.146 | OC₂H₅ | Cl | n = 0 | H | |
| 2.147 | OC₂H₅ | Cl | 3-Cl | H | |
| 2.148 | OC₂H₅ | Cl | 3-F | H | |
| 2.149 | OC₂H₅ | CH₃ | 3-Cl | H | |
| 2.150 | cyclo-C₃H₅ | F | n = 0 | H | |
| 2.151 | cyclo-C₃H₅ | F | 3-Cl | H | |
| 2.152 | cyclo-C₃H₅ | F | 3-F | H | |
| 2.153 | cyclo-C₃H₅ | CH₃ | n = 0 | H | |
| 2.154 | cyclo-C₃H₅ | CH₃ | 3-Cl | H | |
| 2.155 | cyclo-C₃H₅ | CH₃ | 3-F | H | |
| 2.156 | cyclo-C₃H₅ | CH₃ | 3-F,5-F | H | |
| 2.157 | OC₃H₇ | Cl | n = 0 | H | |
| 2.158 | OC₃H₇ | Cl | 3-Cl | H | |
| 2.159 | OC₃H₇ | Cl | 3-F | H | |
| 2.160 | OC₃H₇-i | Cl | n = 0 | H | |
| 2.161 | OC₃H₇-i | Cl | 3-Cl | H | |
| 2.162 | OC₃H₇-i | Cl | 3-F | H | |
| 2.163 | cyclo-C₄H₇ | Cl | n = 0 | H | |
| 2.164 | cyclo-C₄H₇ | Cl | 3-Cl | H | |
| 2.165 | cyclo-C₄H₇ | F | n = 0 | H | |
| 2.166 | cyclo-C₄H₇ | F | 3-Cl | H | |
| 2.167 | cyclo-C₅H₉ | Cl | n = 0 | H | |
| 2.168 | cyclo-C₅H₉ | Cl | 3-Cl | H | |
| 2.169 | cyclo-C₅H₉ | Cl | 3-F | H | |
| 2.170 | cyclo-C₅H₉ | F | n = 0 | H | |
| 2.171 | cyclo-C₅H₉ | F | 3-Cl | H | |
| 2.172 | cyclo-C₅H₉ | F | 3-F | H | |
| 2.173 | cyclo-C₆H₁₁ | Cl | n = 0 | H | |
| 2.174 | cyclo-C₆H₁₁ | Cl | 3-Cl | H | |
| 2.175 | cyclo-C₆H₁₁ | Cl | 3-F | H | |
| 2.176 | C₂H₅ | Cl | n = 0 | C₂H₅ | |
| 2.177 | C₂H₅ | F | n = 0 | C₂H₅ | |
| 2.178 | C₂H₅ | Br | n = 0 | C₂H₅ | |
| 2.179 | C₂H₅ | Cl | 3-Cl | C₂H₅ | |
| 2.180 | C₂H₅ | Cl | 3-F | C₂H₅ | |

TABLE 2-continued

| Comp. No. | R₁ | R₂ | (R₃)ₙ | R₄ | Physical Data |
|---|---|---|---|---|---|
| 2.181 | C₂H₅ | Cl | n = 0 | CH₃ | |
| 2.182 | C₃H₇ | Br | 3-F,5-F | H | |
| 2.183 | C₃H₇ | Br | 3-Cl | H | |
| 2.184 | R₁ + R₄: —(CH₂)₃— | Cl | n = 0 | | |
| 2.185 | R₁ + R₄: —(CH₂)₃— | Cl | 3-Cl | | |
| 2.186 | R₁ + R₄: —(CH₂)₃— | F | n = 0 | | |
| 2.187 | R₁ + R₄: —(CH₂)₃— | F | 3-Cl | | |
| 2.188 | R₁ + R₄: —(CH₂)₃— | F | 3-F | | |
| 2.189 | R₁ + R₄: —(CH₂)₃— | CH₃ | n = 0 | | |
| 2.190 | R₁ + R₄: —(CH₂)₃— | CH₃ | 3-Cl | | |
| 2.191 | R₁ + R₄: —(CH₂)₃— | CH₃ | 3-F | | |
| 2.192 | R₁ + R₄: —(CH₂)₄— | Cl | n = 0 | | |
| 2.193 | R₁ + R₄: —(CH₂)₄— | F | n = 0 | | |
| 2.194 | R₁ + R₄: —(CH₂)₄— | Br | n = 0 | | |
| 2.195 | R₁ + R₄: —(CH₂)₄— | CH₃ | n = 0 | | |
| 2.196 | R₁ + R₄: —(CH₂)₄— | CH₃ | 3-Cl | | |
| 2.197 | C₃H₇ | Br | n = 0 | H | |
| 2.198 | R₁ + R₄: —(CH₂)₅— | Cl | n = 0 | | |
| 2.199 | R₁ + R₄: —(CH₂)₅— | CH₃ | n = 0 | | |
| 2.200 | R₁ + R₄: —(CH₂)₅— | F | n = 0 | | |
| 2.201 | R₁ + R₄: —(CH₂)₅— | F | 3-Cl | | |
| 2.202 | R₁ + R₄: —CH₂CH₂CH=CH— | Cl | n = 0 | | |
| 2.203 | R₁ + R₄: —CH₂CH₂CH=CH— | Cl | 3-F | | |
| 2.204 | R₁ + R₄: —CH₂CH₂CH=CH— | Cl | 3-Cl | | |
| 2.205 | R₁ + R₄: —CH₂OCH₂— | Cl | n = 0 | | |
| 2.206 | R₁ + R₄: —CH₂OCH₂— | Cl | 3-F | | |
| 2.207 | R₁ + R₄: —CH₂OCH₂— | Cl | 3-Cl | | |
| 2.208 | R₁ + R₄: —CH₂OCH₂— | F | n = 0 | | |
| 2.209 | R₁ + R₄: —CH₂OCH₂— | F | 3-Cl | | |
| 2.210 | R₁ + R₄: —CH₂CH₂OCH₂CH₂— | Cl | n = 0 | | |
| 2.211 | R₁ + R₄: —CH₂CH₂OCH₂CH₂— | Cl | 3-Cl | | |
| 2.212 | R₁ + R₄: —CH₂CH₂OCH₂CH₂— | Cl | 3-F | | |
| 2.213 | R₁ + R₄: —CH₂CH(CH₃)OCH₂CH₂— | Cl | n = 0 | | |
| 2.214 | R₁ + R₄: —CH₂CH(CH₃)OCH₂CH₂— | Cl | 3-Cl | | |
| 2.215 | C₂H₅ | C₂H₅ | n = 0 | H | |
| 2.216 | C₂H₅ | C₂H₅ | 3-Cl | H | |
| 2.217 | C₂H₅ | C₂H₅ | 3-F | H | |
| 2.218 | C₂H₅ | C₂H₅ | 3-F,5-F | H | |
| 2.219 | C₂H₅ | C₃H₇ | n = 0 | H | |
| 2.220 | C₂H₅ | C₃H₇ | 3-Cl | H | |
| 2.221 | C₂H₅ | C₃H₇ | 3-F | H | |
| 2.222 | C₂H₅ | i-C₃H₇ | n = 0 | H | |
| 2.223 | C₂H₅ | i-C₃H₇ | 3-Cl | H | |
| 2.224 | C₂H₅ | i-C₃H₇ | 3-F | H | |
| 2.225 | C₃H₇ | i-C₃H₇ | n = 0 | H | |
| 2.226 | C₃H₇ | i-C₃H₇ | 3-Cl | H | |
| 2.227 | C₂H₅ | CF₃ | n = 0 | H | |
| 2.228 | C₂H₅ | CF₃ | 3-Cl | H | |
| 2.229 | C₂H₅ | CF₃ | 3-F | H | |
| 2.230 | C₃H₇ | CF₃ | n = 0 | H | |
| 2.231 | C₃H₇ | CF₃ | 3-Cl | H | |
| 2.232 | C₃H₇ | CF₃ | 3-F | H | |
| 2.233 | CH₃ | OCH₃ | n = 0 | H | |
| 2.234 | CH₃ | OCH₃ | 3-Cl | H | |
| 2.235 | C₂H₅ | OCH₃ | n = 0 | H | |

TABLE 2-continued

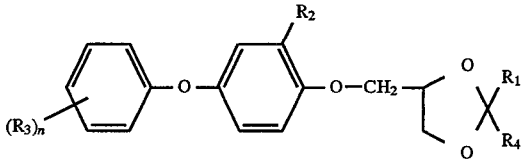

| Comp. No. | $R_1$ | $R_2$ | $(R_3)_n$ | $R_4$ | Physical Data |
|---|---|---|---|---|---|
| 2.236 | $C_2H_5$ | $OCH_3$ | 3-Cl | H | |
| 2.237 | $C_2H_5$ | $OCH_3$ | 3-F | H | |
| 2.238 | $C_3H_7$ | $OCH_3$ | n = 0 | H | |
| 2.239 | $C_3H_7$ | $OCH_3$ | 3-Cl | H | |
| 2.240 | $C_3H_7$ | $OCH_3$ | 3-F,5-F | H | |
| 2.241 | ethynyl | Cl | n = 0 | H | |
| 2.242 | ethynyl | Cl | 3-F | H | |
| 2.243 | ethynyl | Cl | 3-F,5-F | H | |
| 2.244 | $C_2H_5$ | Br | 3-F,5-F | H | |
| 2.245 | $CH_3$ | $OCF_3$ | n = 0 | $CH_3$ | |
| 2.246 | $CH_3$ | $OCF_3$ | n = 0 | H | |
| 2.247 | $CH_3$ | $OCF_3$ | 3-Cl | H | |
| 2.248 | $C_2H_5$ | $OCH_3$ | n = 0 | H | |
| 2.249 | $C_2H_5$ | $OCF_3$ | 3-Cl | H | |
| 2.250 | $C_2H_5$ | $OCF_3$ | 3-F | H | |
| 2.251 | $C_2H_5$ | $OCF_3$ | 3-F,5-F | H | |
| 2.252 | $C_3H_7$ | $OCF_3$ | n = 0 | H | |
| 2.253 | $C_3H_7$ | $OCF_3$ | 3-Cl | H | |
| 2.254 | $C_3H_7$ | $OCF_3$ | 3-F | H | |
| 2.255 | $CH_3$ | F | n = 0 | $CH_3$ | |
| 2.256 | $CH_3$ | F | n = 0 | H | |
| 2.257 | $CH_3$ | F | 3-F | H | |
| 2.258 | $CH_3$ | F | 3-Cl | H | |
| 2.259 | $C_2H_5$ | F | 3-F,5-F | H | |
| 2.260 | $C_2H_5$ | F | 3-$CH_3$ | H | |
| 2.261 | $C_2H_5$ | F | 4-$CH_3$ | H | |
| 2.262 | $C_2H_5$ | F | n = 0 | H | |
| 2.263 | $C_3H_7$ | F | 3-F,5-F | H | |
| 2.264 | $C_3H_7$ | F | 3-$CH_3$ | H | |
| 2.265 | $C_3H_7$ | F | 4-$CH_3$ | H | |
| 2.266 | $C_2H_5$ | Br | 3-Cl | H | |
| 2.267 | $CH_3$ | Br | n = 0 | $CH_3$ | |
| 2.268 | $CH_3$ | Br | n = 0 | H | |
| 2.269 | $CH_3$ | Br | 3-Cl | H | |
| 2.270 | $CH_3$ | Br | 3-F | H | |
| 2.271 | $-CH=CHCH_3$ (E/Z) | F | n = 0 | H | |

TABLE 3

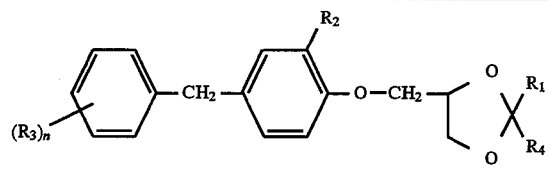

| Comp. No. | $R_1$ | $R_2$ | $(R_3)_n$ | $R_4$ | Physical Data |
|---|---|---|---|---|---|
| 3.1 | $CH_3$ | Cl | n = 0 | $CH_3$ | $n_D^{20} = 1.5554$ |
| 3.2 | $CH_3$ | Cl | n = 0 | H | |
| 3.3 | $C_2H_5$ | Cl | n = 0 | H | |
| 3.3.1 | $C_2H_5$ | Cl | n = 0 | H | A; $n_D^{20} = 1.5573$ |
| 3.3.2 | $C_2H_5$ | Cl | n = 0 | H | B; $n_D^{20} = 1.5587$ |
| 3.4 | $C_3H_7$ | Cl | n = 0 | H | |
| 3.4.1 | $C_3H_7$ | Cl | n = 0 | H | A; $n_D^{20} = 1.5524$ |
| 3.4.2 | $C_3H_7$ | Cl | n = 0 | H | B; $n_D^{20} = 1.5533$ |
| 3.5 | i-$C_3H_7$ | Cl | n = 0 | H | |
| 3.5.1 | i-$C_3H_7$ | Cl | n = 0 | H | A; $n_D^{20} = 1.5512$ |
| 3.5.2 | i-$C_3H_7$ | Cl | n = 0 | H | B; $n_D^{20} = 1.5522$ |
| 3.6 | cyclo-$C_3H_5$ | Cl | n = 0 | H | |
| 3.6.1 | cyclo-$C_3H_5$ | Cl | n = 0 | H | A; $n_D^{20} = 1.5670$ |
| 3.6.2 | cyclo-$C_3H_5$ | Cl | n = 0 | H | B; $n_D^{20} = 1.5682$ |
| 3.7 | i-$C_4H_9$ | Cl | n = 0 | H | |
| 3.8 | $C_2H_5$ | $CH_3$ | n = 0 | H | |
| 3.9 | i-$C_3H_7$ | $CH_3$ | n = 0 | H | |

TABLE 3-continued

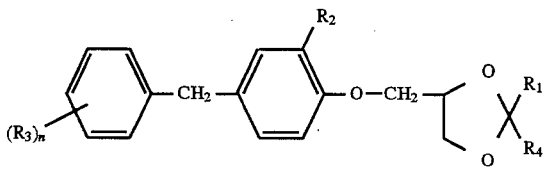

| Comp. No. | $R_1$ | $R_2$ | $(R_3)_n$ | $R_4$ | Physical Data |
|---|---|---|---|---|---|
| 3.10 | cyclo-$C_3H_5$ | $CH_3$ | n = 0 | H | |
| 3.11 | $CH_3$ | Cl | 3-F | $CH_3$ | |
| 3.12 | $CH_3$ | Cl | 3-F | H | |
| 3.12.1 | $CH_3$ | Cl | 3-F | H | A; $n_D^{20}$ = 1.5530 |
| 3.12.2 | $CH_3$ | Cl | 3-F | H | B; $n_D^{20}$ = 1.5549 |
| 3.13 | $C_2H_5$ | Cl | 3-F | H | |
| 3.13.1 | $C_2H_5$ | Cl | 3-F | H | A; $n_D^{20}$ = 1.5481 |
| 3.13.2 | $C_2H_5$ | Cl | 3-F | H | B; $n_D^{20}$ = 1.5490 |
| 3.14 | $C_3H_7$ | Cl | 3-F | H | |
| 3.14.1 | $C_3H_7$ | Cl | 3-F | H | A; $n_D^{20}$ = 1.5439 |
| 3.14.2 | $C_3H_7$ | Cl | 3-F | H | B; $n_D^{20}$ = 1.5452 |
| 3.15 | i-$C_3H_7$ | Cl | 3-F | H | |
| 3.16 | cyclo-$C_3H_5$ | Cl | 3-F | H | |
| 3.17 | i-$C_4H_9$ | Cl | 3-F | H | |
| 3.18 | $C_4H_9$ | $CH_3$ | 3-F | H | |
| 3.19 | $CH_3$ | Cl | 3-F,5-F | $CH_3$ | |
| 3.20 | $CH_3$ | Cl | 3-F,5-F | H | |
| 3.21 | $C_2H_5$ | Cl | 3-F,5-F | H | |
| 3.21.1 | $C_2H_5$ | Cl | 3-F,5-F | H | A; $n_D^{20}$ = 1.5401 |
| 3.21.2 | $C_2H_5$ | Cl | 3-F,5-F | H | B; $n_D^{20}$ = 1.5409 |
| 3.22 | $C_3H_7$ | Cl | 3-F,5-F | H | |
| 3.23 | i-$C_3H_7$ | Cl | 3-F,5-F | H | |
| 3.24 | cyclo-$C_3H_5$ | Cl | 3-F,5-F | H | |
| 3.25 | i-$C_4H_9$ | Cl | 3-F,5-F | H | |
| 3.26 | $C_2H_5$ | Cl | 3-Cl,4-Cl | H | |
| 3.26.1 | $C_2H_5$ | Cl | 3-Cl,4-Cl | H | A; m.p. = 86–87° |
| 3.26.2 | $C_2H_5$ | Cl | 3-Cl,4-Cl | H | B; m.p. = 66–67° |
| 3.27 | $C_3H_7$ | Cl | 3-Cl,4-Cl | H | |
| 3.27.1 | $C_3H_7$ | Cl | 3-Cl,4-Cl | H | A; m.p. = 52–53° |
| 3.27.2 | $C_3H_7$ | Cl | 3-Cl,4-Cl | H | B; m.p. = 58–59° |
| 3.28 | cyclo-$C_3H_5$ | Cl | 3-Cl,4-Cl | H | |
| 3.28.1 | cyclo-$C_3H_5$ | Cl | 3-Cl,4-Cl | H | A; $n_D^{20}$ = 1.5808 |
| 3.28.2 | cyclo-$C_3H_5$ | Cl | 3-Cl,4-Cl | H | B; $n_D^{20}$ = 1.5820 |
| 3.29 | $C_2H_5$ | Br | 3-Cl,4-Cl | H | m.p. = 70–72° |
| 3.30 | $C_2H_5$ | Br | n = 0 | H | |
| 3.30.1 | $C_2H_5$ | Br | n = 0 | H | A; $n_D^{20}$ = 1.5701 |
| 3.30.2 | $C_2H_5$ | Br | n = 0 | H | B; $n_D^{20}$ = 1.5718 |
| 3.31 | i-$C_3H_7$ | Br | n = 0 | H | |
| 3.31.1 | i-$C_3H_7$ | Br | n = 0 | H | A; $n_D^{20}$ = 1.5630 |
| 3.31.2 | i-$C_3H_7$ | Br | n = 0 | H | B; $n_D^{20}$ = 1.5641 |
| 3.32 | $C_2H_5$ | F | 3-F | H | |
| 3.32.1 | $C_2H_5$ | F | 3-F | H | A; $n_D^{20}$ = 1.5304 |
| 3.32.2 | $C_2H_5$ | F | 3-F | H | B; $n_D^{20}$ = 1.5311 |
| 3.33 | $C_3H_7$ | F | 3-F | H | |
| 3.33.1 | $C_3H_7$ | F | 3-F | H | A; m.p. = 47–48° |
| 3.33.2 | $C_3H_7$ | F | 3-F | H | B; $n_D^{20}$ = 1.5269 |
| 3.34 | ethynyl | Cl | n = 0 | H | $n_D^{20}$ = 1.5695 |
| 3.35 | $CH_3$ | Cl | 3-$CF_3$ | $CH_3$ | |
| 3.36 | $CH_3$ | Cl | 3-Cl | H | |
| 3.37 | $CH_3$ | Cl | 3-$CH_3$ | H | |
| 3.38 | $C_2H_5$ | Cl | 3-F,4-Cl | H | |
| 3.39 | $C_2H_5$ | Cl | 3-Cl | H | |
| 3.40 | $C_2H_5$ | Cl | 3-$CH_3$ | H | |
| 3.41 | $C_2H_5$ | Cl | 3-$OCH_3$ | H | |
| 3.42 | $C_2H_5$ | Cl | 3-$CF_3$ | H | |
| 3.43 | $C_2H_5$ | Cl | 3-$OCF_3$ | H | |
| 3.44 | $C_2H_5$ | Cl | 4-F | H | |
| 3.45 | $C_2H_5$ | Cl | 3-Cl,5-Cl | H | |
| 3.46 | $C_3H_7$ | Cl | 3-Cl | H | |
| 3.47 | $C_3H_7$ | Cl | 3-$CH_3$ | H | |
| 3.48 | $C_3H_7$ | Cl | 3-$C_2H_5$ | H | |
| 3.49 | $C_3H_7$ | Cl | 3-$OCH_3$ | H | |
| 3.50 | $C_3H_7$ | Cl | 3-$CF_3$ | H | |
| 3.51 | $C_3H_7$ | Cl | 3-$OCF_3$ | H | |
| 3.52 | $C_3H_7$ | Cl | 4-F | H | |
| 3.53 | i-$C_3H_7$ | Cl | 3-Cl | H | |
| 3.54 | i-$C_3H_7$ | Cl | 3-$CH_3$ | H | |
| 3.55 | i-$C_3H_7$ | Cl | 3-$C_2H_5$ | H | |

TABLE 3-continued

Structure: (R₃)ₙ—C₆H₄—CH₂—C₆H₃(R₂)—O—CH₂—CH(dioxolane with R₁, R₄)

| Comp. No. | R₁ | R₂ | (R₃)ₙ | R₄ | Physical Data |
|---|---|---|---|---|---|
| 3.56 | C₂H₅ | F | n = 0 | H | |
| 3.57 | C₂H₅ | F | 3-Cl | H | |
| 3.58 | C₂H₅ | F | 3-F,5-F | H | |
| 3.59 | C₃H₇ | F | n = 0 | H | |
| 3.60 | C₃H₇ | F | 3-Cl | H | |
| 3.61 | cyclo-C₃H₅ | Cl | 3-Cl | H | |
| 3.62 | cyclo-C₃H₅ | Cl | 3-CH₃ | H | |
| 3.63 | i-C₄H₉ | Cl | 3-Cl | H | |
| 3.64 | i-C₄H₉ | Cl | 3-CH₃ | H | |
| 3.65 | C₆H₁₃ | Cl | n = 0 | H | |
| 3.66 | C₆H₁₃ | Cl | 3-Cl | H | |
| 3.67 | —CH=CH₂ | Cl | n = 0 | H | |
| 3.68 | —CH=CH₂ | Cl | 3-Cl | H | |
| 3.69 | —CH=CH₂ | Cl | 3-F | H | |
| 3.70 | —CH=CH₂ | Cl | 3-F,5-F | H | |
| 3.71 | ethynyl | Cl | 3-Cl | H | |
| 3.72 | ethynyl | Cl | 3-F | H | |
| 3.73 | ethynyl | Cl | 3-F,5-F | H | |
| 3.74 | prop-1-yn-1-yl | Cl | n = 0 | H | |
| 3.75 | prop-1-yn-1-yl | Cl | 3-Cl | H | |
| 3.76 | prop-1-yn-1-yl | Cl | 3-F | H | |
| 3.77 | prop-1-en-1-yl | Cl | n = 0 | H | |
| 3.78 | prop-1-en-1-yl | Cl | 3-Cl | | |
| 3.79 | prop-1-en-1-yl | Cl | 3-F | H | |
| 3.80 | —CH=C(CH₃)₂ | Cl | n = 0 | H | |
| 3.81 | —CH=C(CH₃)₂ | Cl | 3-Cl | H | |
| 3.82 | —CH=C(CH₃)₂ | Cl | 3-F | H | |
| 3.83 | CH₃ | CH₃ | n = 0 | CH₃ | |
| 3.84 | CH₃ | CH₃ | 3-Cl | CH₃ | |
| 3.85 | CH₃ | CH₃ | n = 0 | H | |
| 3.86 | CH₃ | CH₃ | 3-Cl | H | |
| 3.87 | CH₃ | CH₃ | 3-F | H | |
| 3.88 | C₂H₅ | CH₃ | 3-Cl | H | |
| 3.89 | C₂H₅ | CH₃ | 3-F | H | |
| 3.90 | C₂H₅ | CH₃ | 3-F,5-F | H | |
| 3.91 | C₂H₅ | CH₃ | 3-C₂H₅ | H | |
| 3.92 | C₃H₇ | CH₃ | n = 0 | H | |
| 3.93 | C₃H₇ | CH₃ | 3-Cl | H | |
| 3.94 | C₃H₇ | CH₃ | 3-F | H | |
| 3.95 | C₃H₇ | CH₃ | 3-F,5-F | H | |
| 3.96 | C₃H₇ | CH₃ | 3-CH₃ | H | |
| 3.97 | i-C₃H₇ | CH₃ | 3-Cl | H | |
| 3.98 | i-C₃H₇ | CH₃ | 3-F | H | |
| 3.99 | cyclo-C₃H₅ | CH₃ | 3-Cl | H | |
| 3.100 | cyclo-C₃H₅ | CH₃ | 3-F | H | |
| 3.101 | —CH=CH₂ | CH₃ | n = 0 | H | |
| 3.102 | —CH=CH₂ | CH₃ | 3-Cl | H | |
| 3.103 | —CH=CH₂ | CH₃ | 3-F | H | |
| 3.104 | ethynyl | CH₃ | n = 0 | H | |
| 3.105 | ethynyl | CH₃ | 3-Cl | H | |
| 3.106 | ethynyl | CH₃ | 3-F | H | |
| 3.107 | R₁ + R₄: —(CH₂)₃— | Cl | n = 0 | | |
| 3.108 | R₁ + R₄: —(CH₂)₃— | Cl | 3-F | | |
| 3.109 | R₁ + R₄: —(CH₂)₃— | Cl | 3-Cl | | |
| 3.110 | R₁ + R₄: —(CH₂)₄— | Cl | n = 0 | | |
| 3.111 | R₁ + R₄: —(CH₂)₄— | Cl | 3-F | | |
| 3.112 | R₁ + R₄: —(CH₂)₄— | Cl | 3-Cl | | |
| 3.113 | R₁ + R₄: —(CH₂)₅— | Cl | n = 0 | | |
| 3.114 | R₁ + R₄: —(CH₂)₅— | Cl | 3-F | | |
| 3.115 | R₁ + R₄: —(CH₂)₅— | Cl | 3-CH₃ | | |
| 3.116 | R₁ + R₄: —CH₂OCH₂CH₂CH₂— | Cl | n = 0 | | |
| 3.117 | R₁ + R₄: —CH₂OCH₂CH₂CH₂— | Cl | 3-F | | |
| 3.118 | R₁ + R₄: —CH₂OCH₂CH₂CH₂— | Cl | 3-Cl | | |
| 3.119 | C₂H₅ | CF₃ | n = 0 | H | |
| 3.120 | C₂H₅ | CF₃ | 3-Cl | H | |

TABLE 3-continued

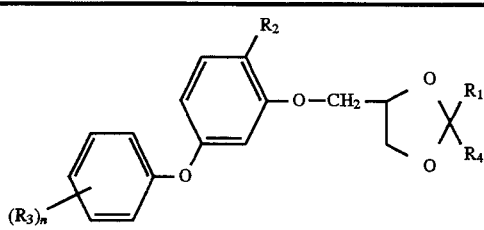

| Comp. No. | $R_1$ | $R_2$ | $(R_3)_n$ | $R_4$ | Physical Data |
|---|---|---|---|---|---|
| 3.121 | $C_2H_5$ | $CF_3$ | 3-F | H | |
| 3.122 | $C_3H_7$ | $CF_3$ | n = 0 | H | |
| 3.123 | $C_3H_7$ | $CF_3$ | 3-Cl | H | |
| 3.124 | $C_3H_7$ | $CF_3$ | 3-F | H | |
| 3.125 | $C_2H_5$ | $OCH_3$ | n = 0 | H | |
| 3.126 | $C_2H_5$ | $OCH_3$ | 3-Cl | H | |
| 3.127 | $C_2H_5$ | $OCH_3$ | 3-F | H | |
| 3.128 | $OCH_3$ | Cl | n = 0 | $CH_3$ | |
| 3.129 | $OCH_3$ | Cl | 3-Cl | $CH_3$ | |
| 3.130 | $OCH_3$ | Cl | 3-F | $CH_3$ | |
| 3.131 | $OCH_3$ | Cl | 3-F,5-F | H | |
| 3.132 | $OC_2H_5$ | Cl | n = 0 | H | |
| 3.133 | $OC_2H_5$ | Cl | 3-Cl | H | |
| 3.134 | $OC_2H_5$ | Cl | 3-F | H | |
| 3.135 | $OC_2H_5$ | Cl | 3-F,5-F | H | |
| 3.136 | $OC_2H_5$ | Cl | 3-$CH_3$ | H | |
| 3.137 | $OCH(CH_3)_2$ | Cl | n = 0 | H | |
| 3.138 | $OCH(CH_3)_2$ | Cl | 3-Cl | H | |
| 3.139 | $OCH(CH_3)_2$ | Cl | 3-F | H | |
| 3.140 | $OCH_2CH_2CH_3$ | Cl | n = 0 | H | |
| 3.141 | $OCH_2CH_2CH_3$ | Cl | 3-Cl | H | |
| 3.142 | $OCH_2CH_2CH_3$ | Cl | 3-F | H | |
| 3.143 | $OCH_3$ | Br | n = 0 | H | |
| 3.144 | $OCH_3$ | Br | 3-Cl | H | |
| 3.145 | $OCH_3$ | Br | 3-F | H | |
| 3.146 | $OC_2H_5$ | Br | n = 0 | H | |
| 3.147 | $OC_2H_5$ | Br | 3-Cl | H | |
| 3.148 | $OC_2H_5$ | Br | 3-Br | H | |
| 3.149 | $OCH_3$ | F | n = 0 | H | |
| 3.150 | $OCH_3$ | F | 3-Cl | H | |
| 3.151 | $OCH_3$ | F | 3-F | H | |
| 3.152 | $OC_2H_5$ | F | n = 0 | H | |
| 3.153 | $OC_2H_5$ | F | 3-Cl | H | |
| 3.154 | $OC_2H_5$ | F | 3-Br | H | |
| 3.155 | $OCH_3$ | $CH_3$ | n = 0 | H | |
| 3.156 | $OCH_3$ | $CH_3$ | 3-Cl | H | |
| 3.157 | $OCH_3$ | $CH_3$ | 3-Br | H | |
| 3.158 | $OCH_3$ | $CH_3$ | 3-F | H | |
| 3.159 | $OC_2H_5$ | $CH_3$ | n = 0 | H | |
| 3.160 | $OC_2H_5$ | $CH_3$ | 3-Cl | H | |
| 3.161 | $OC_2H_5$ | $CH_3$ | 3-F | H | |

TABLE 4

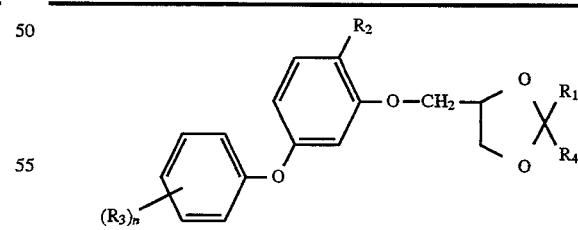

| Comp. No. | $R_1$ | $R_2$ | $(R_3)_n$ | $R_4$ | Physical data |
|---|---|---|---|---|---|
| 4.1 | $C_2H_5$ | Cl | 3-Cl | H | $n_D^{20}$ = 1.5662 |
| 4.2 | $C_3H_7$ | Cl | 3-Cl | H | $n_D^{20}$ = 1.5609 |
| 4.3 | $CH_3$ | Cl | n = 0 | $CH_3$ | |
| 4.4 | $CH_3$ | Cl | n = 0 | H | |
| 4.5 | $CH_3$ | Cl | 3-Cl | H | |
| 4.6 | $CH_3$ | Cl | 3-F | H | |
| 4.7 | $C_2H_5$ | Cl | n = 0 | H | |
| 4.8 | $C_2H_5$ | Cl | 3-F | H | |
| 4.9 | $C_2H_5$ | Cl | 3-F,5-F | H | |
| 4.10 | $C_2H_5$ | Cl | 3-$CH_3$ | H | |
| 4.11 | $C_3H_7$ | Cl | n = 0 | H | |
| 4.12 | $C_3H_7$ | Cl | 3-F | H | |
| 4.13 | $C_3H_7$ | Cl | 3-F,5-F | H | |
| 4.14 | i-$C_3H_7$ | Cl | n = 0 | H | |
| 4.15 | i-$C_3H_7$ | Cl | 3-Cl | H | |
| 4.16 | i-$C_3H_7$ | Cl | 3-F | H | |

TABLE 4-continued

![Structure: (R3)n-phenyl-O-phenyl(R2)-O-CH2-C(R1)(R4) dioxolane]

| Comp. No. | R₁ | R₂ | (R₃)ₙ | R₄ | Physical data |
|---|---|---|---|---|---|
| 4.17 | cyclo-C₃H₅ | Cl | n = 0 | H | |
| 4.18 | cyclo-C₃H₅ | Cl | 3-F | H | |
| 4.19 | cyclo-C₃H₅ | Cl | 3-Cl | H | |
| 4.20 | cyclo-C₃H₅ | Cl | 3-F,5-F | H | |
| 4.21 | C₂H₅ | Br | n = 0 | H | |
| 4.22 | C₂H₅ | Br | 3-Cl | H | |
| 4.23 | C₂H₅ | Br | 3-F | H | |
| 4.24 | C₃H₇ | Br | n = 0 | H | |
| 4.25 | C₃H₇ | Br | 3-Cl | H | |
| 4.26 | C₃H₇ | Br | 3-F | H | |
| 4.27 | C₂H₅ | CH₃ | n = 0 | H | |
| 4.28 | C₂H₅ | CH₃ | 3-Cl | H | |
| 4.29 | C₂H₅ | CH₃ | 3-F | H | |
| 4.30 | C₂H₅ | CH₃ | 3-F,5-F | H | |
| 4.31 | C₃H₇ | CH₃ | n = 0 | H | |
| 4.32 | C₃H₇ | CH₃ | 3-Cl | H | |
| 4.33 | C₃H₇ | CH₃ | 3-F | H | |

TABLE 5

![Structure: (R3)n-phenyl-O-phenyl(R2)-O-CH2-C(R5)(R1)(R4) dioxolane]

| Comp. No. | R₁ | R₂ | (R₃)ₙ | R₄ | R₅ | Physical Data |
|---|---|---|---|---|---|---|
| 5.1 | C₂H₅ | Cl | 3-F | H | CH₃ | |
| 5.2 | CH₃ | Cl | n = 0 | H | CH₃ | |
| 5.3 | CH₃ | Cl | n = 0 | CH₃ | CH₃ | |
| 5.4 | CH₃ | Cl | 3-Cl | H | CH₃ | |
| 5.5 | CH₃ | Cl | 3-F | H | CH₃ | |
| 5.6 | C₂H₅ | Cl | n = 0 | H | CH₃ | |
| 5.7 | C₂H₅ | Cl | 3-Cl | H | CH₃ | |
| 5.8 | C₂H₅ | Cl | 3-F,5-F | H | CH₃ | |
| 5.9 | C₃H₇ | Cl | n = 0 | H | CH₃ | |
| 5.10 | C₃H₇ | Cl | 3-Cl | H | CH₃ | |
| 5.11 | C₃H₇ | Cl | 3-F | H | CH₃ | |
| 5.12 | C₃H₇ | Cl | 3-F,5-F | H | CH₃ | |
| 5.13 | cyclo-C₃H₅ | Cl | n = 0 | H | CH₃ | |
| 5.14 | cyclo-C₃H₅ | Cl | 3-Cl | H | CH₃ | |
| 5.15 | cyclo-C₃H₅ | Cl | 3-F | H | CH₃ | |
| 5.16 | i-C₃H₇ | Cl | n = 0 | H | CH₃ | |
| 5.17 | i-C₃H₇ | Cl | 3-Cl | H | CH₃ | |
| 5.18 | i-C₃H₇ | Cl | 3-F | H | CH₃ | |
| 5.19 | C₂H₅ | F | n = 0 | H | CH₃ | |
| 5.20 | C₂H₅ | F | 3-Cl | H | CH₃ | |
| 5.21 | C₂H₅ | F | 3-F | H | CH₃ | |
| 5.22 | C₂H₅ | F | 3-F,5-F | H | CH₃ | |
| 5.23 | C₃H₇ | F | n = 0 | H | CH₃ | |
| 5.24 | C₃H₇ | F | 3-Cl | H | CH₃ | |
| 5.25 | C₃H₇ | F | 3-F | H | CH₃ | |
| 5.26 | i-C₄H₉ | F | n = 0 | H | CH₃ | |
| 5.27 | i-C₄H₉ | F | 3-Cl | H | CH₃ | |
| 5.28 | C₂H₅ | CH₃ | n = 0 | H | CH₃ | |
| 5.29 | C₂H₅ | CH₃ | 3-Cl | H | CH₃ | |
| 5.30 | C₂H₅ | CH₃ | 3-F | H | CH₃ | |
| 5.31 | C₂H₅ | CH₃ | 3-F,5-F | H | CH₃ | |
| 5.32 | C₃H₇ | CH₃ | n = 0 | H | CH₃ | |

TABLE 5-continued

![Structure]

| Comp. No. | R₁ | R₂ | (R₃)ₙ | R₄ | R₅ | Physical Data |
|---|---|---|---|---|---|---|
| 5.33 | C₃H₇ | CH₃ | 3-Cl | H | CH₃ | |
| 5.34 | C₃H₇ | CH₃ | 3-F | H | CH₃ | |
| 5.35 | C₃H₇ | CH₃ | 3-F,5-F | H | CH₃ | |
| 5.36 | C₂H₅ | Cl | n = 0 | H | C₂H₅ | |
| 5.37 | C₂H₅ | Cl | 3-Cl | H | C₂H₅ | |
| 5.38 | C₂H₅ | Cl | 3-F | H | C₂H₅ | |
| 5.39 | C₂H₅ | Cl | n = 0 | H | C₃H₇ | |
| 5.40 | C₂H₅ | Cl | 3-Cl | H | C₃H₇ | |
| 5.41 | C₂H₅ | Cl | 3-F | H | C₃H₇ | |

TABLE 6

![Structure: (R3)n-phenyl-CH2-phenyl(R2)-O-CH2-C(R5)(R1)(R4) dioxolane]

| Comp. No. | R₁ | R₂ | (R₃)ₙ | R₄ | R₅ | Physical Data |
|---|---|---|---|---|---|---|
| 6.1 | C₃H₇ | CH₃ | 3-F | H | CH₃ | |
| 6.2 | C₃H₇ | CH₃ | 3-Cl | H | CH₃ | |
| 6.3 | CH₃ | Cl | n = 0 | CH₃ | CH₃ | |
| 6.4 | CH₃ | Cl | n = 0 | H | CH₃ | |
| 6.5 | C₂H₅ | Cl | n = 0 | H | CH₃ | |
| 6.6 | C₂H₅ | Cl | 3-Cl | H | CH₃ | |
| 6.7 | C₂H₅ | Cl | 3-F | H | CH₃ | |
| 6.8 | C₂H₅ | Cl | 3-F,5-F | H | CH₃ | |
| 6.9 | C₂H₅ | CH₃ | n = 0 | H | CH₃ | |
| 6.10 | C₂H₅ | CH₃ | 3-Cl | H | CH₃ | |
| 6.11 | C₂H₅ | CH₃ | 3-F | H | CH₃ | |
| 6.12 | C₂H₅ | Br | n = 0 | H | CH₃ | |
| 6.13 | C₂H₅ | Br | 3-Cl | H | CH₃ | |
| 6.14 | C₂H₅ | Br | 3-F | H | CH₃ | |
| 6.15 | C₂H₅ | F | n = 0 | H | CH₃ | |
| 6.16 | C₂H₅ | F | 3-Cl | H | CH₃ | |
| 6.17 | C₂H₅ | F | 3-F | H | CH₃ | |
| 6.18 | C₂H₅ | F | 4-F | H | CH₃ | |
| 6.19 | C₂H₅ | F | 3-F,5-F | H | CH₃ | |
| 6.20 | C₃H₇ | Cl | n = 0 | H | CH₃ | |
| 6.21 | C₃H₇ | Cl | 3-Cl | H | CH₃ | |
| 6.22 | C₃H₇ | Cl | 3-F | H | CH₃ | |
| 6.23 | C₃H₇ | Cl | 3-F,5-F | H | CH₃ | |
| 6.24 | C₃H₇ | CH₃ | n = 0 | H | CH₃ | |

TABLE 7

![Structure: (R3)n-phenyl-C(=O)-phenyl(R2)-O-CH2-C(R1)(R4) dioxolane]

| Comp. No. | R₁ | R₂ | (R₃)ₙ | R₄ | Physical Data |
|---|---|---|---|---|---|
| 7.1 | cyclo-C₃H₅ | Cl | n = 0 | H | |
| 7.1.1 | cyclo-C₃H₅ | Cl | n = 0 | H | A; $n_D^{20}$ = 1.5825 |

TABLE 7-continued

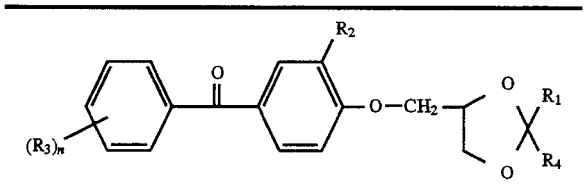

| Comp. No. | $R_1$ | $R_2$ | $(R_3)_n$ | $R_4$ | Physical Data |
|---|---|---|---|---|---|
| 7.1.2 | cyclo-$C_3H_5$ | Cl | n = 0 | H | B; $n_D^{20}$ = 1.5859 |
| 7.2 | $C_2H_5$ | Cl | n = 0 | H | $n_D^{20}$ = 1.5811 |
| 7.3 | $C_3H_7$ | Cl | 4-Cl | H | |
| 7.3.1 | $C_3H_7$ | Cl | 4-Cl | H | A; m.p. = 74–75° |
| 7.3.2 | $C_3H_7$ | Cl | 4-Cl | H | B; m.p. = 83–84° |
| 7.4 | $C_2H_5$ | Cl | 4-Cl | H | |
| 7.4.1 | $C_2H_5$ | Cl | 4-Cl | H | A; m.p. = 100–101° |
| 7.4.2 | $C_2H_5$ | Cl | 4-Cl | H | B; m.p. = 101–102° |
| 7.5 | $CH_3$ | Cl | n = 0 | $CH_3$ | |
| 7.6 | $CH_3$ | Cl | n = 0 | H | |
| 7.7 | $CH_3$ | Cl | 3-Cl | H | |
| 7.8 | $CH_3$ | Cl | 3-F | H | |
| 7.9 | $C_2H_5$ | Cl | 3-Cl | H | |
| 7.10 | $C_2H_5$ | Cl | 3-F | H | |
| 7.11 | $C_3H_7$ | Cl | 3-Cl | H | |
| 7.12 | $C_3H_7$ | Cl | 3-F | H | |
| 7.13 | $C_2H_5$ | Br | n = 0 | H | |
| 7.14 | $C_2H_5$ | Br | 3-Cl | H | |
| 7.15 | $C_2H_5$ | Br | 3-F | H | |

TABLE 8

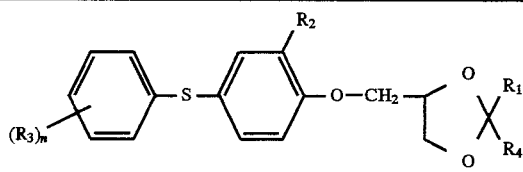

| Comp. No. | $R_1$ | $R_2$ | $(R_3)_n$ | $R_4$ | Physical Data |
|---|---|---|---|---|---|
| 8.1 | $CH_3$ | Cl | n = 0 | $CH_3$ | |
| 8.2 | $CH_3$ | Cl | 3-Cl | $CH_3$ | |
| 8.3 | $CH_3$ | Cl | 3-F | $CH_3$ | |
| 8.4 | $CH_3$ | Cl | n = 0 | H | |
| 8.5 | $CH_3$ | Cl | 3-Cl | H | |
| 8.6 | $CH_3$ | Cl | 3-F | H | |
| 8.7 | $CH_3$ | Cl | 3-F,5-F | H | |
| 8.8 | $C_2H_5$ | Cl | n = 0 | H | |
| 8.9 | $C_2H_5$ | Cl | 3-$CF_3$ | H | |
| 8.10 | $C_2H_5$ | Cl | 3-Cl | H | |
| 8.11 | $C_2H_5$ | Cl | 3-F | H | |
| 8.12 | $C_2H_5$ | Cl | 3-F,5-F | H | |
| 8.13 | $C_3H_7$ | Cl | n = 0 | H | |
| 8.14 | $C_3H_7$ | Cl | 3-Cl | H | |
| 8.15 | $C_3H_7$ | Cl | 3-F | H | |
| 8.16 | cyclo-$C_3H_5$ | Cl | n = 0 | H | |
| 8.17 | cyclo-$C_3H_5$ | Cl | 3-Cl | H | |
| 8.18 | cyclo-$C_3H_5$ | Cl | 3-F | H | |
| 8.19 | i-$C_3H_7$ | Cl | n = 0 | H | |
| 8.20 | i-$C_3H_7$ | Cl | 3-Cl | H | |
| 8.21 | i-$C_3H_7$ | Cl | 3-F | H | |
| 8.22 | i-$C_4H_9$ | Cl | n = 0 | H | |
| 8.23 | i-$C_4H_9$ | Cl | 3-Cl | H | |
| 8.24 | i-$C_4H_9$ | Cl | 3-F | H | |
| 8.25 | $C_2H_5$ | Br | n = 0 | R | |
| 8.26 | $C_2H_5$ | Br | 3-Cl | H | |
| 8.27 | $C_2H_5$ | Br | 3-F | H | |
| 8.28 | $C_3H_7$ | Br | n = 0 | H | |
| 8.29 | $C_3H_7$ | Br | 3-Cl | H | |
| 8.30 | $C_3H_7$ | Br | 3-F | H | |

Example H5

The compound of the formula II which is listed in Table 9 can also be prepared analogously to the procedure described in Example H1, if desired after additional purification by chromatography [$CH_2Cl_2$/$(C_2H_5)_2O$=3:2].

TABLE 9

| Comp. No. | $R_2$ | $(R_3)_n$ | Physical Data |
|---|---|---|---|
| 9.1 | Cl | 3-Cl | $n_D^{20}$ = 1.5909 |

Formulation Examples

| Example F1: Emulsion concentrates | a) | b) | c) |
|---|---|---|---|
| Active ingredient according to Preparation Examples | 25% | 40% | 50% |
| Calcium dodecylbenzenesulfonate | 5% | 8% | 6% |
| Castor oil polyethylene glycol ether (36 mol EO) | 5% | — | — |
| Tributylphenol polyethylene glycol ether (30 mol EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient according to Preparation Examples | 80% | 10% | 5% | 95% |
| Ethylene glycol monomethyl ether | 20% | — | — | — |
| Polyethylene glycol (MW 400) | — | 70% | — | — |
| N-Methyl-2-pyrrolidone | — | 20% | — | — |
| Epoxidised coconut oil | — | — | 1% | 5% |
| Petroleum spirit (boiling range: 160–190° C.) | — | — | 94% | — |

The solutions are suitable for use in the form of microdrops.

| Example F3: Granules | a) | b) |
|---|---|---|
| Active ingredient according to Preparation Examples | 5% | 10% |
| Kaolin | 94% | — |
| Highly disperse silica | 1% | — |
| Attapulgite | — | 90% |

The active ingredient is dissolved in dichloromethane, the solution is sprayed onto the carrier, and the solvent is subsequently removed by evaporation in vacuo.

| Example F4: Dusts | a) | b) |
|---|---|---|
| Active ingredient according to Preparation Examples | 2% | 5% |
| Highly disperse silica | 1% | 5% |
| Talc | 97% | — |
| Kaolin | — | 90% |

Ready-for-use dusts are obtained by intimately mixing the carriers with the active ingredient.

| Example F5: Wettable powders | a) | b) | c) |
|---|---|---|---|
| Active ingredient according to Preparation Examples | 20% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 mol EO) | — | 2% | — |
| Highly disperse silica | 5% | 10% | 10% |
| Kaolin | 67% | 27% | — |

The active ingredient is mixed thoroughly with the additives, and the mixture is ground thoroughly in a suitable mill. This gives wettable powders which can be diluted with water to give suspensions of any desired concentration.

| Example F6: Emulsion concentrate | a) | b) |
|---|---|---|
| Active ingredient according to Preparation Examples | 10% | 10% |
| Octylphenol polyethylene glyol ether (4–5 mol EO) | 3% | — |
| Calcium dodecylbenzenesulfonate | 3% | — |
| Castor oil polyglycol ether (36 mol EO) | 4% | — |
| Castor oil thioxylate | — | 25% |
| Cyclohexanone | 30% | — |
| Butanol | — | 15% |
| Xylene mixture | 50% | — |
| Ethyl acetate | — | 50% |

Emulsions of any desired concentration can be prepared from these concentrates by dilution with water.

| Example F7: Dusts | a) | b) |
|---|---|---|
| Active ingredient according to Preparation Examples | 5% | 8% |
| Talc | 95% | — |
| Kaolin | — | 92% |

Ready-for-use dusts are obtained by mixing the active ingredient with the carrier and grinding the mixture in a suitable mill.

| Example F8: Extruder granules | |
|---|---|
| Active ingredient according to Preparation Examples | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| Example F9: Coated granules | |
|---|---|
| Active ingredient according to Preparation Examples | 3% |
| Polyethylene glycol (MW 200) | 3% |
| Kaolin | 94% |

In a mixer, the finely-ground active ingredient is applied uniformly to the kaolin which has been moistened with polyethylene glycol. Dust-free coated granules are obtained in this manner.

| Example F10: Suspension concentrate | |
|---|---|
| Active ingredient according to Preparation Examples | 40% |
| Ethylene glycol | 10% |
| Nonylphenol polyethylene glycol ether (15 mol EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired concentration can be prepared by dilution with water.

Biological Examples

EXAMPLE B1

Activity against *Boophilus microplus*

Adult ticks (females) which have sucked themselves full are stuck onto a PVC plate and covered with a cottonwool ball. For the treatment, 10 ml of an aqueous test solution comprising 125 ppm of the active ingredient to be tested are poured over the test animals. The cottonwool ball is subsequently removed, and the ticks are incubated for 4 weeks for oviposition. The activity against *Boophilus microplus* becomes apparent either in the female in the form of mortality or sterility, or in the eggs in the form of an ovicidal activity.

In this test, compounds of Tables 2 to 8 have a good activity.

EXAMPLE B2

Ovicidal activity on *Cydia pomonella*

*Cydia pomonella* eggs which have been deposited on filter paper are briefly immersed into a test solution comprising 400 ppm of the active ingredient to be tested in acetone/water. After the test solution has dried on, the eggs are incubated in Petri dishes. After 6 days, the hatching percentage of the eggs is evaluated by comparison with untreated control batches (% hatching reduction).

In this test, compounds of Tables 2 to 8 have a good activity.

EXAMPLE B3

Ovicidal activity on *Adoxophyes reticulana*

*Adoxophyes reticulana* eggs which have been deposited on filter paper are briefly immersed into a test solution comprising 400 ppm of the active ingredient to be tested in acetone/water. After the test solution has dried on, the eggs are incubated in Petri dishes. After 6 days, the hatching percentage of the eggs is evaluated by comparison with untreated control batches (% hatching reduction).

In this test, compounds of Tables 2 to 8 have a good activity.

EXAMPLE B4

Ovicidal activity on *Lobesia botrana*

*Lobesia botrana* eggs which have been deposited on filter paper are briefly immersed into a test solution comprising 400 ppm of the active ingredient to be tested in acetone/water. After the test solution has dried on, the eggs are incubated in Petri dishes. After 6 days, the hatching percentage of the eggs is evaluated by comparison with untreated control batches (% hatching reduction).

In this test, compounds of Tables 2 to 8 have a good activity.

EXAMPLE B5

Activity against *Aonidiella aurantii*

Potato tubers are populated with *Aonidiella aurantii* (orange scale insect) crawlers. After approx. 2 weeks, the potatoes are immersed in an aqueous emulsion, or suspension, spray mixture comprising the active ingredient to be tested at a concentration of 400 ppm. After the treated potato tubers have dried, they are incubated in a plastic container. To evaluate the test, the survival rate of the crawlers of the first subsequent generation of the treated scale insect population is compared after 10–12 weeks with that of the untreated control batches.

In this test, compounds of Tables 2 to 8 have a good activity.

EXAMPLE B6

Activity against *Nilaparvata lugens*

Rice plants are treated with an aqueous emulsion spray mixture comprising 400 ppm of the active ingredient. After the spray coating has dried on, the rice plants are populated with *cicada larvae* of the 2nd and 3rd stage. The test is evaluated 21 days later. The percentage reduction in population (% activity) is determined by comparing the number of surviving cicadas on the treated with the number of surviving cicadas on the untreated plants.

In this test, compounds of Tables 2 to 8 have a good activity.

EXAMPLE B7

Activity against *Nephotettix cincticeps*

Rice plants are treated with an aqueous emulsion spray mixture comprising 400 ppm of the active ingredient. After the spray coating has dried on, the rice plants are populated with *cicada larvae* of the 2nd and 3rd stage. The test is evaluated 21 days later. The percentage reduction in population (% activity) is determined by comparing the number of surviving cicadas on the treated with the number of surviving cicadas on the untreated plants.

In this test, compounds of Tables 2 to 8 have a good activity.

EXAMPLE B8

Activity against *Bemisia tabaci*

Dwarf bean plants are placed into gauze cages and populated with *Bemisia tabaci* (whitefly) adults. When oviposition has taken place, all adults are removed, and, 10 days later, the plants together with the nymphs with which they are populated are treated with an aqueous emulsion spray mixture of the active ingredients to be tested (concentration 400 ppm). The test is evaluated 14 days after the active ingredient has been applied by determining the hatching percentage in comparison with the untreated control batches. In this test, compounds of Tables 2 to 8 have a good activity.

EXAMPLE B9

Activity against *Tetranychus urticae*

Young bean plants are populated with a mixed population of *Tetranychus urticae*, and, 1 day later, sprayed with an aqueous emulsion spray mixture comprising 400 ppm of the active ingredient. The plants are subsequently incubated for 6 days at 25° C. and then evaluated. The percentage reduction in population (% activity) is determined by comparing the number of dead eggs, larvae and adults on the treated plants with the number of dead eggs, larvae and adults on the untreated plants.

In this test, compounds of Tables 2 to 8 have a good activity.

EXAMPLE B10

Ovo/larvicidal activity on *Heliothis virescens*

*Heliothis virescens* eggs which have been deposited on cotton are sprayed with an aqueous emulsion spray mixture comprising 400 ppm of the active ingredient. After 8 days, the hatching percentage of the eggs and the survival rate of the caterpillars are evaluated by comparing them with untreated control batches (% reduction in population).

In this test, compounds of Tables 2 to 8 have a good activity.

EXAMPLE B11

Activity against *Panonychus ulmi* (OP- and Carb.-resistant)

Apple seedlings are populated with adult *Panonychus ulmi* females. After seven days, the infected plants are sprayed to drip point with an aqueous emulsion spray mixture comprising 400 ppm of the compound to be tested and grown in the greenhouse. The test is evaluated after 14 days. The percentage population reduction (% activity) is determined by comparing the number of dead spider mites on the treated plants with the number of dead spider mites on the untreated plants.

In this test, compounds of Tables 2 to 8 have a good activity.

EXAMPLE B12

Activity against *Ctenocephalides felis*

20 to 25 flea eggs are placed into a horizontally positioned 50 ml cell culture flask into which 15 g of flea larvae medium comprising 100 ppm of the active ingredient to be tested had been introduced. The test flasks are incubated in an incubator at 26° to 27° C. and 60–70% atmospheric humidity. The presence of adult fleas, unhatched pupae and larvae is checked after 21 days.

In this test, compounds of Tables 2 to 8 have a good activity.

EXAMPLE B13

Activity against *Bemisia tabaci* eggs

Dwarf bean plants are placed into gauze cages and populated with *Bemisia tabaci* (whitefly) adults. When oviposition has taken place, all adults are removed, and, 2 days later, the plants together with the nymphs with which they are populated are treated with an aqueous emulsion spray mixture of the active ingredients to be tested (concentration 400 ppm). The test is evaluated 10 days after the active ingredient has been applied by determining the hatching percentage in comparison with the untreated control batches.

In this test, compounds of Tables 2 to 8 have a good activity.

What is claimed is:

1. A compound of the formula

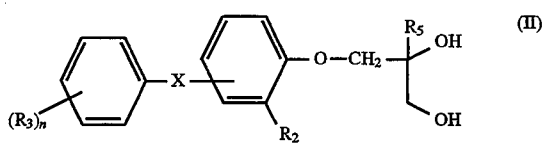

(II)

in which:

n is 0, 1 or 2, and, if n is 2, the two radicals $R_3$ are identical or different;

$R_2$ is methyl, fluorine, chlorine or bromine;

$R_3$ is $C_1$–$C_3$alkyl, halo-$C_1$–$C_3$alkyl, $C_1$–$C_3$alkoxy, halo-$C_1$–$C_3$alkoxy, fluorine, chlorine or bromine;

$R_5$ is hydrogen or $C_1$–$C_3$alkyl and

X is O.

2. A compound according to claim 1 of the formula (II), wherein $R_2$ is fluorine or chlorine;

$R_3$ is fluorine or chlorine;

$R_5$ is hydrogen and

X is O.

3. A compound according to claim 1 of the formula (II), wherein $R_2$ is chlorine;

$R_3$ is fluorine or chlorine;

$R_5$ is hydrogen and

X is O.

4. A compound according to claim 1 of the formula (II), wherein $R_2$ is bromine;

$R_3$ is fluorine or chlorine;

$R_5$ is hydrogen and

X is O.

* * * * *